(12) United States Patent
Marth et al.

(10) Patent No.: US 8,034,556 B2
(45) Date of Patent: Oct. 11, 2011

(54) REGULATION OF GLUCOSE AND INSULIN LEVELS BY GNT-4 GLYCOSYLTRANSFERASE ACTIVITY

(75) Inventors: Jamey Marth, San Diego, CA (US); Kazuaki Ohtsubo, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1044 days.

(21) Appl. No.: 11/569,655

(22) PCT Filed: May 27, 2005

(86) PCT No.: PCT/US2005/018910
§ 371 (c)(1),
(2), (4) Date: Nov. 27, 2006

(87) PCT Pub. No.: WO2005/117950
PCT Pub. Date: Dec. 15, 2005

(65) Prior Publication Data
US 2007/0259379 A1  Nov. 8, 2007

Related U.S. Application Data

(60) Provisional application No. 60/575,785, filed on May 28, 2004.

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS
5,968,764 A  10/1999  Knowles et al.

OTHER PUBLICATIONS

Van Tilburg et al. (2003) J. Clin. Endo. Metab. 88: 2223-2230.*
Asano et al.; "The role of N-glycosylation in the targeting and stability of GLUT1 glucose transporter"; *FEBS Lett.*; 324(3):258-61 (Jun. 1993).
Asano et al.; "The role of N-glycosylation of GLUT1 for glucose transport"; *J. Biol. Chem.*; 266(36):24632-24636-61 (1991).
Gremlich et al.; "Dexamethasone induces posttranslational degradation of GLUT2 and inhibition of insulin secretion in isolated pancreatic beta cells. Comparison with the effects of fatty acids"; *J. Biol. Chem.*; 272(6):3216-3222 (1997).
Joos et al.; "The extended GLUT-family of sugar/polyol transport facilitators: nomenclature, sequence characteristics, and potential function of its novel members"; *Mol. Membr. Biol.*; 18(4):247-256; (2001).
Lowe et al.; "A genetic approach to Mammalian glycan function"; *Ann. Rev. Biochem.*; 72:643-691 (epub Mar. 2003).
Uldry et al.; "The SLC2 family of facilitated hexose and polyol transporters"; *Pflugers Arch—Eur J Physiol*; 447:480-489 (Apr. 2004).
Uldry et al.; "The SLC2 family of facilitated hexose and polyol transporters"; *Pflugers Arch—Eur J Physiol*; 448(2):259-260 *erratum* (May 2004).
Yoshida et al.; "Tissue specific expression and chromosomal mapping of a human UDP-N-acetylglucosamine: alpha1,3-d-mannoside beta1,4-N-acetylglucosaminyltransferase"; *Glycobiology*; 9(3):303-310 (1999).
International Search Report and Written Opinion from PCT/US05/18910, dated Mar. 16, 2009 (9 pages).

* cited by examiner

*Primary Examiner* — Michael Pak
(74) *Attorney, Agent, or Firm* — Kilpatrick Townsend & Stockton LLP

(57) ABSTRACT

The invention is based on the discovery that the gylcosylation enzyme GnT-4 increases glyocsylation and the stability of glucose transporter (Glut) family members, e.g., by increasing lectin binding. Modulators of GnT-4 activity can therefore be identified and used for the treatment of diabetes or pre-diabetes. In addition, inhibitors of GnT-4 activity can be used for the treatment of cancer.

1 Claim, 6 Drawing Sheets

US 8,034,556 B2

REGULATION OF GLUCOSE AND INSULIN LEVELS BY GNT-4 GLYCOSYLTRANSFERASE ACTIVITY

CROSS-REFERENCES TO RELATED APPLICATIONS

Figure 1:
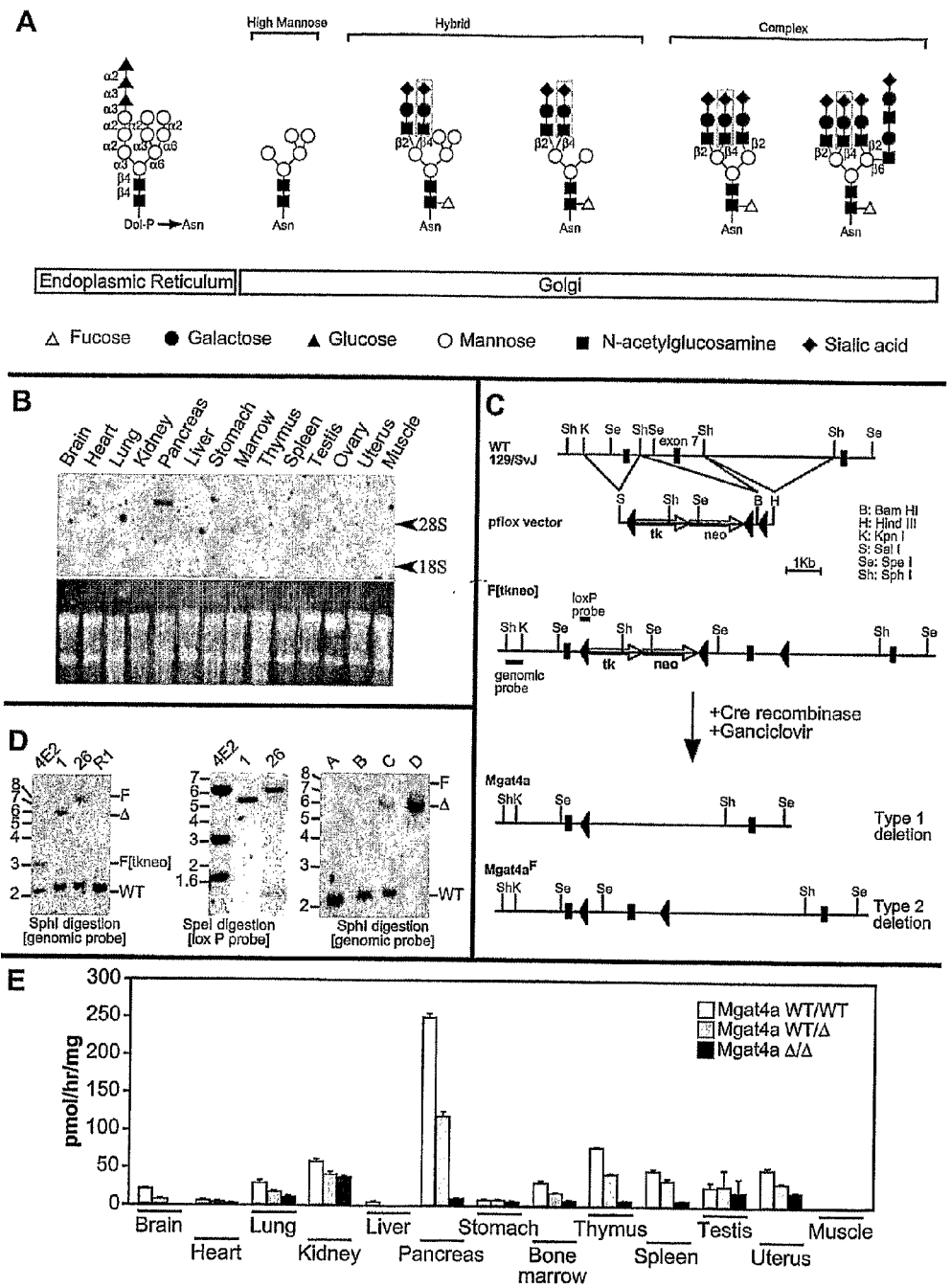

This application claims benefit of U.S. provisional patent application No. 60/575,785, filed May 28, 2004, which is incorporated by reference herein.

STATEMENT AS TO RIGHTS TO INVENTIONS MADE UNDER FEDERALLY SPONSORED RESEARCH OR DEVELOPMENT

This invention was made with Government support under Grant No. IDK48247, awarded by the National Institutes of Health. The Government has certain rights in this invention.

BACKGROUND OF THE INVENTION

The regulated secretion of insulin by the pancreatic beta cell modulates blood glucose levels within a limited range that facilitates normal metabolism. Increased glucose concentrations are sensed upon transport across the plasma membrane by Glucose Transporter glycoprotein resulting in insulin secretion. Activation of insulin receptors on various cell types diminishes circulating glucose levels by increasing glucose uptake and utilization, and reducing gluconeogenesis in the liver. Failures within this regulatory network can result in diabetes and associated pathologic syndromes that affect a large and growing percentage of the human population.

Glucose Transporters (Gluts) are a family of transmembrane glycoproteins expressed differentially among cell types and bearing distinct affinities for glucose and other saccharide ligands. One or more Glut family members are required by all viable cells to support cellular energy requirements in quiescent and activated metabolism. Altered Glut expression or transporter function may contribute the etiology of metabolic syndromes. For example, reduced pancreatic Glut-2 expression to 10% of normal in mice using an antisense-RNA approach was reported to induce diabetes. In normal contexts, pancreatic beta cell Glut-2 is expressed predominantly at the cell surface and is not sequestered among intracellular compartments. However, decreased Glut-2 expression and intracellular accumulation have been observed in animal models of diabetes, and following administration of a high-fat diet. Glut transporter deficiency at the cell surface attenuates the beta cell response to increased glucose concentrations, resulting in deficient insulin secretion and chronic hyperglycemia that may exacerbate the development of insulin resistance. Post-translational modification of Glut expression may contribute to a mechanism underlying normal glucose homeostasis and the etiology of diabetes.

The post-translational modification of Glut-2 includes a single N-glycosylation site conserved among all homologues of vertebrate species studied. N-glycans that reach the mammalian cell surface are typically multi-branched structures produced in the Golgi apparatus by sequential saccharide linkage formation by glycosyltransferase enzymes. N-glycan branching forms the necessary scaffolding for the construction of saccharide linkage patterns that can operate as ligands for lectin receptors. With the exception of the N-glycan branch initiated by β-4 linked N-acetylglucosamine addition, other major N-glycan branch structures have been assigned specific biologic functions in humans and mice, and in some cases, roles in genetic disease (Lowe and Marth, *Annu Rev Biochem.* 72:643-91, 2003).

Mannosyl (α-1,3-)-glycoprotein beta-1,4-N-acetylglucosaminyltransferase (also referred to as Mgat 4 or GnT-4) is involved in N-glycan synthesis. For example, the Mgat4a-encoded GnT-4a initiates the β-4 linked N-acetylglucosamine branch on the α-3 linked core mannose (FIG. 1A). The mouse Mgat4a gene is highly conserved and selectively expressed among normal tissues and cell types, with highest levels in the pancreas and intestinal tract (FIG. 1B). The present invention is based, in part, on the discovery of dietary regulation of β-4 linked N-acetylglucosamine branch expression on Glut-2 and a role for this N-glycan structure in controlling pancreatic glucose transport and insulin secretion.

BRIEF SUMMARY OF THE INVENTION

The present invention provides methods of regulating the level of Glut, e.g., Glut-1, -2, -3, or -4. In some embodiments Glut-1 or Glut-2 expression on pancreatic beta cells is regulated. The invention is based, at least in part, on the discovery that expression of Mgat4a promotes Glut-2 activity on the beta cell plasma membrane, increasing glucose uptake and insulin secretion. With impaired Mgat4a expression, development of type II diabetes occurs. The data presented here show that in an established animal model deficient in Mgat4a expression, Glut-2 levels are decreased.

Enhancing levels of Mgat4 expression in type II diabetes and other metabolic diseases can be used to treat disease. Alternatively, Mgat4 expression or gene product activity can be inhibited using standard techniques (e.g., RNAi, small molecule inhibitors, and the like) to reduce Glut function and thereby inhibit cellular proliferation (e.g., in cancer cells).

This invention therefore provides methods to treat diabetes by regulating the levels of glycosylation of Glut polypeptides, which affects Glut stability and thus, levels of Glut. The levels of Glut polypeptides (e.g., Glut 1-4) can therefore be increased by enhancing GnT-4 expression, e.g., enhancing Mgat4a expression, or delivering the gene product of Mgat4, e.g, Mgat4a. The mechanism of Mgat4-deficient type 2 diabetes involves a reduction in pancreatic β-cell surface expression of glucose transporter, e.g., Glut-2, coincident with accumulation of intracellular Glut, e.g., Glut-2. There is presently no other reported mechanism for regulating Glut, e.g., Glut-2 expression. Mgat4a codes for a glycosyltransferase that post translationally modifies pancreatic Glut-2. One embodiment of the invention is gene or protein therapy using Mgat4. Alternatively, β-cells engineered to express an Mgat4 gene can be administered to patients with diabetes.

There is also considerable literature showing that enzyme activity of the Mgat4 gene product (also known as GnT-4) is increased substantially in many types of cancers. The invention therefore also provide methods of treating cancer by inhibiting the level of Glut glycosylation and thus, the stability of Glut, thereby decreasing glucose transport that is required to achieve the higher metabolic rate found in cancer.

Thus, in one aspect, the invention provides a method of identifying an agent for the treatment of a diabetic or prediabetic individual, the method comprising identifying a candidate agent that increases Glut binding to a lectin. In some embodiments, the Glut is expressed by a pancreatic β-cell. The Glut can be any Glut, but is typically a member of the Glut-1, -2, -3, and -4 subfamily. Often, the Glut is Glut-2 or Glut-1.

In some embodiments, the method comprises identifying a candidate agent that increases the binding affinity of Glut to lectin. A candidate agent can be an antibody, such as a bispecific antibody.

In one embodiment, the step of identifying the candidate agent comprises identifying an agent that increases the level of Glut N-glycosylation. In some embodiments, the agent can increase N- acetylglucosaminyltransferase-4 (GnT-4) activity. In exemplary embodiments, the agent increases GnT-4 activity by increasing the level of GnT-4 protein and/or mRNA expression.

The method can further comprise a step of validating the compound in a mammalian model of diabetes. In exemplary validation steps, the compound is evaluated for the ability to increase insulin secretion and/or decrease blood glucose levels.

In another aspect, the invention provides a method of identifying an agent for the treatment of a diabetic or pre-diabetic individual, the method comprising identifying a candidate agent that stabilizes Glut on a pancreatic cell surface, wherein the candidate agent increases the amount of Glut glycosylation, e.g., the oligosaccharide Galβ4GlcNAcβ4Man branch (i.e., enhances the synthesis of the Galβ4GlcNAcβ4Man-containing oligosaccharide branch shown in the shaded area of FIG. 1). The candidate agent can, e.g., increase the activity of any enzyme involve in the synthesis of the oligosaccharide. In preferred embodiments, it is involved in the synthesis of the Galβ4GlcNAcβ4Man-containing branch. The enzyme can be, e.g., an N-acetylglucosaminytransferase, such as Gnt-4, a galactosyltransferase, or a mannose transferase. In one embodiment, the step of identifying the candidate agent comprises contacting the candidate agent with Glut; determining the level of Glut binding to a lectin; and selecting the agent that increases Glut binding to lectin.

The invention also includes a method of identifying an agent for the treatment of a diabetic or pre-diabetic individual, the method comprising identifying an agent that competes with a lectin for specific binding to Glut. In some embodiments, the method is performed in vitro.

In another aspect the invention provides a method of increasing the stability of Glut at a cell surface, e.g., the surface of a pancreatic islet cell, by administering an agent that increases Glut binding to lectin. Such a method can be used, e.g., for the treatment of diabetes. In some embodiments, the agent increases the level of Glut N-glycosylation. For example, the agent can increase glycosyltransferase activity, such as GnT-4 activity, by increasing mRNA or protein expression of the glycosyltransferase.

The invention additionally provides a method of increasing the level of Glut glycosylation in a pancreatic islet cell, the method comprising introducing into a pancreatic islet cell, or a stem cell that differentiates into a pancreatic islet cell, an expression vector comprising a nucleic acid that encodes a GnT-4 polypeptide, e.g., a polypeptide that comprises the amino acid sequence set forth in SEQ ID NO:2 or SEQ ID NO:4. The expression vector can be introduced into the islet cell or stem cell in vitro. Alternatively, the expression vector can be administered to pancreatic tissue in vivo.

The invention also provides an isolated pancreatic islet cell or an isolated stem cell comprising an expression vector that encodes a GnT-4 polypeptide, e.g., a GnT-4 polypeptide comprising the amino acid sequence of SEQ ID NO:2 or SEQ ID NO:4.

In another aspect, the invention provides a method of treating an individual with diabetes or pre-diabetes, the method comprising administering an agent that inhibits sialyl transferase to pancreatic tissue. In some embodiments, the agent is an siRNA.

The invention also provides a method of identifying an increased risk for diabetes, the method comprising identifying a mutation in an Mgat4 gene, where the mutation decreases activity of GnT-4. The invention also provides a method of identifying an increased risk for diabetes, the method comprising identifying a mutation in a sialyltransferase where the mutation leads to aberrant sialic acid at terminal linkage positions of the Glut tetra-antennary branch structure shown in FIG. 1A.

In another aspect, the invention provides a method of identifying an agent that inhibits growth of a cancer cell, the method comprising identifying a candidate agent that decreases Glut binding, e.g, Glut-2 binding, to a lectin. In some embodiments, the method comprises identifying a candidate agent that decreases the binding affinity of Glut to a lectin or that competes with binding of Glut to a lectin. In particular embodiments, the agent is an antibody.

In some embodiments the step of identifying the candidate agent comprises identifying an agent that decreases the level of Glut N-glycosylation. The agent can, for example, decrease a glycosyltransferase activity, e.g., GnT-4 activity. In some embodiments, the activity is decreased by decreasing protein or mRNA expression of the gycosyltransferase, e.g., GnT-4.

The method can further comprise a step of administering the agent to a cancer cell and detecting a decrease in cell proliferation.

The invention also provides a method of identifying an agent for the treatment of cancer, the method comprising identifying a candidate agent that decreases Glut stability on a cancer cell surface, wherein the candidate agent decreases the synthesis of the Galβ4GlcNAcβ4Man branch structure depicted in FIG. 1A. In some embodiments, the method comprises a step of identifying the candidate agent comprises contacting the candidate agent with Glut; determining the level of Glut binding to a lectin; and selecting the agent that competes with the lectin for binding to Glut.

In another aspect, the invention relates to a method of inhibiting the proliferation of a cancer cell, the method comprising administering an agent that decreases Glut binding to lectin. The agent can be, for example, an antibody. In other embodiments, the agent decreases the level of Glut N-glycosylation. In particular embodiments, the agent decreases the activity of a glycosyltransferase involved in synthesizing the Galβ4GlcNAcβ4Man-containing branch of a complex oligosaccharide, e.g., that shown in FIG. 1. In some embodiments, the glycosyltransferase is GnT-4, a galactosyltransferase or a mannose transferase. In some embodiments, the agent decreases the level of glyoscyltransferase, e.g., GnT-4 transferase, protein or mRNA expression. In other embodiments, the agent inhibits enzyme activity, e.g., GnT-4 activity.

In another aspect, the invention provides a method of decreasing the level of Glut glycosylation in a cancer cell, the method comprising introducing into the cancer cell a nucleic acid that inhibits glycosyltransferase expression, e.g., GnT-4 expression. Such an agent can be, e.g., an siRNA or antisense nucleic acid.

BRIEF DESCRIPTION OF THE DRAWINGS

FIG. 1. Activity, Expression, and Mutagenesis of the Mgat4a-Encoded GnT-4a Glycosyltransferase. (A) Mammalian N-glycan formation begins in the endoplasmic reticulum with the transfer of the oligosaccharide precursor from lipid to asparagines on nascent peptides, and proceeds in the Golgi apparatus where three major types of mature N-glycan structures can be produced, high-mannose, hybrid, and complex, depending upon the cellular expression profiles of different glycosyltransferases. GnT-4a transfers N-acetylglucosamine in β4 linkage to underlying α3-linked mannose thereby initiating formation of this distinct N-glycan branch (shaded). (B) Expression of Mgat4a RNA transcripts in normal adult mouse total RNA samples from indicated tissues. This result is representative from both males and females at 8 weeks of age (n=6). (C) A mouse genomic clone of Mgat4a bearing exon 6, 7, and 8 (black boxes) was used for constructing the targeting vector with the pflox plasmid as indicated. Homologous recombination produces the Mgat4a F[tk-neo] allele. Following Cre recombination and selection, embryonic stem (ES) cell clones are isolated containing the type 1 (Δ, deleted) and the type 2 (F, floxed) alleles. (D) Genomic Southern blotting confirmed the above Mgat4a allelic structures. Left and middle panels: ES cell clones bearing indicated mutant Mgat4a alleles in comparison with DNA from R1 parental wild-type ES cells. Right panel: Adult mouse genotypes with germline modifications to the Mgat4a gene including Mgat4a$^F$ and Mgat4a$^\Delta$ alleles, the latter produced subsequent to breeding mice bearing the Mgat4a$^F$ allele in a maternal Zp3-Cre transgenic background (Shafi, et al., *Proc. Natl. Acad. Sci. USA* 97:5735-5739, 2001). (E) GnT-4a enzyme activity was decreased to background levels in mice homozygous for the Mgat4a$^\Delta$ allele among all tissues surveyed except for the kidney. Results are expressed as mean±SD (n=3). No change in GnT-4a activity was observed in tissues of mice homozygous for the Mgat4a$^F$ allele (data not shown).

Figure 2:
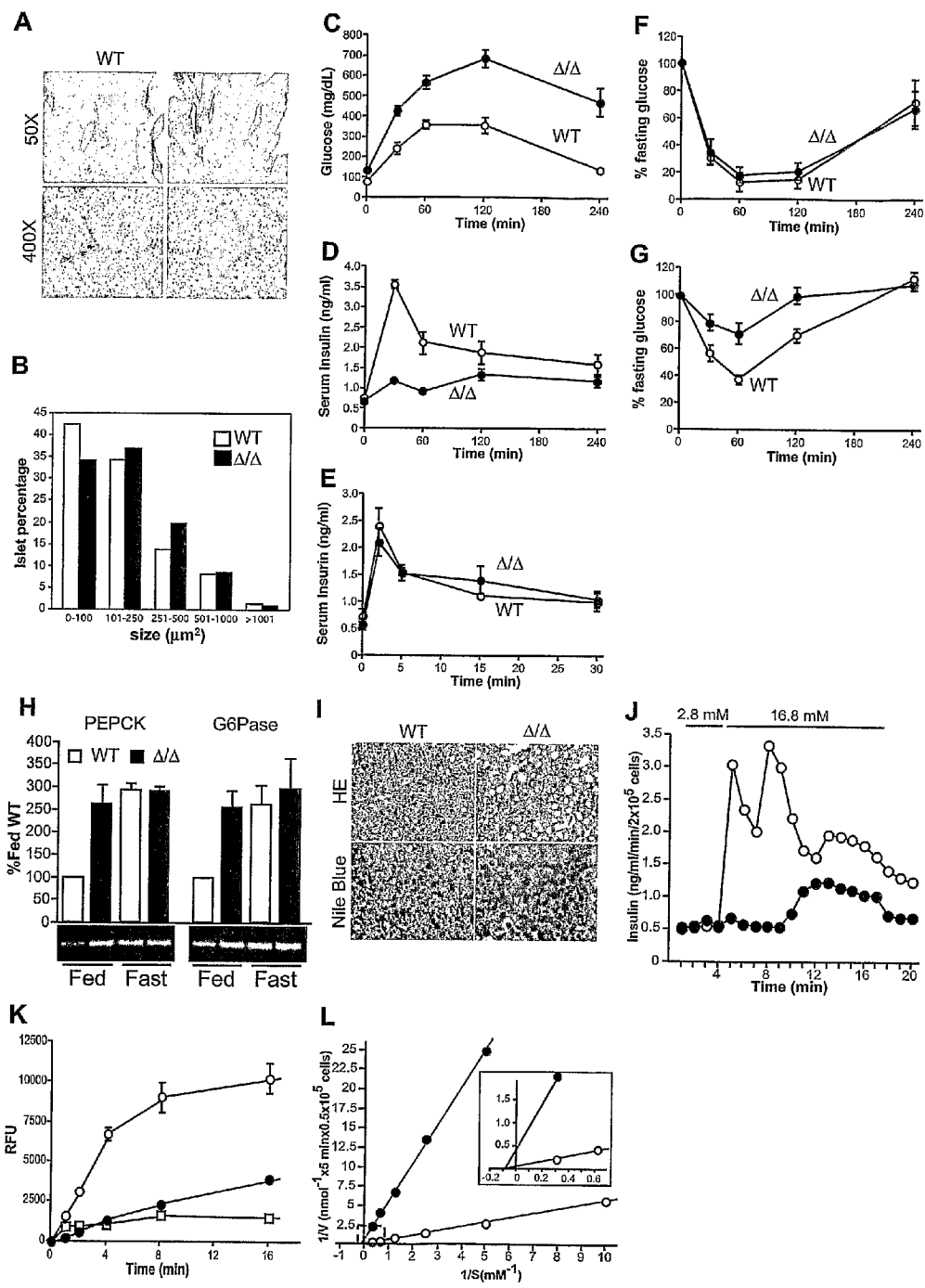

FIG. 2. Type 2 Diabetic Phenotype of Mgat4a-Deficient Mice Associated with Reduced Pancreatic Islet Cell Glucose Uptake and Diminished Insulin Secretion. (A) Insulin visualization with HRP-conjugated secondary antibody in pancreatic sections of wild-type and GnT-4a deficient mice counterstained with hematoxylin. (B) The size and distribution of pancreatic islets were calculated among littermates. Wild-type and Mgat4a null islets averaged 211.74±29.06 mm$^2$ and 234.03±24.22 mm$^2$, respectively (n=6). (C) Glucose tolerance test comparing fasted wild-type (white circles) and Mgat4a null (black circles) littermates (n=10; * p<0.0001). (D) Serum insulin levels measured during the glucose tolerance test (n=10; * p<0.0001). (E) Serum insulin levels following a single injection of L-arginine (n=10). (F, G) Serum glucose levels in mice fasted for 5 hours following insulin injection. The data is graphed as the percent of serum glucose levels pre-insulin treatment in wild-type (white circles) and Mgat4a null (black circles) littermates. Mice (n=10) were aged either 12 weeks (F) or 1 year (G) (**, p<0.001; *, p<0.005). In C-G, results are plotted as the mean±standard error of the mean. (H) PEPCK and G6Pase RNA levels were measured in total RNA samples from liver tissue. The amount of RNA was quantified by the incorporated $^{32}$P, and graphed as a percent of fed wild-type littermate values. (I) Liver tissue sections from 6-month old littermates were stained with hematoxylin and eosin (HE). Lipids were visualized using Nile Blue. Magnification: 200X. (J) In vitro glucose-stimulated insulin secretion. Perifusion was performed in parallel for 2×10$^5$ isolated islet cells from wild-type (white circles) and Mgat4a null (black circles) littermates. The glucose concentration of the perifusate was increased from 2.8 mM to 16.8 mM at 4 minutes. (K) Time course of 2-NBDG glucose analog uptake (500 mM extracellular concentration) by wild-type islet cells in the absence (white circles) and presence (white squares) of 10 mM non-labeled D-glucose, and by Mgat4a null islet cells (black circles). Fluorescence intensities were expressed as relative fluorescence unit (RFU). Data are represented as the means±S.E.M. from three independent experiments. (L) Lineweaver-Burke plot of 2-NBDG uptake by islet cells from wild-type (white circles) and Mgat4a null (black circles) littermates. The Km value for wild-type and Mgat4a null islet cells are 9.525 and 9.104 mM, respectively. Vmax values in nmol/5 min/0.5×10$^5$ cells are 16.95 for wild-type islets, and 1.86 for Mgat4a null islets. All mice used in these studies were 8-12 weeks of age except for those analyzed in panels G, H, and I as indicated.

Figure 3:
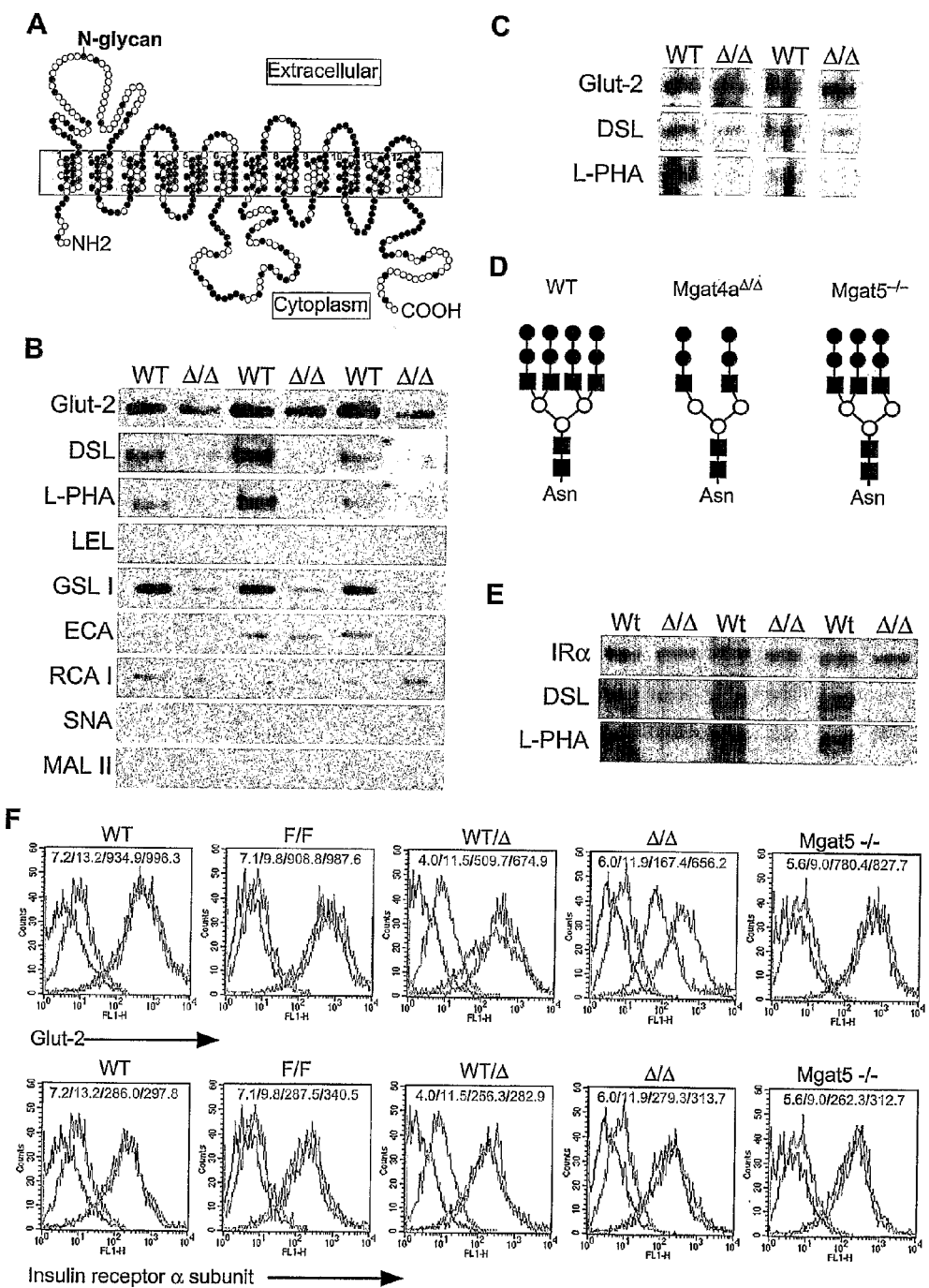

FIG. 3. Glucose Transporter Glut-2 Structure, Glycosylation, and Expression. (A) Conservation and predicted topology of vertebrate Glut-2 glucose transporter homologues. The orientation of Glut-2 in the lipid bilayer (modified from Olson & Pessin, *Annu. Rev. Nutr.* 16: 235-256, 1996) was proposed from its homology to Glut-1 and Glut-4, and by the hydropathy plot of its amino acid sequence (Joost & Thorens, *Mol. Membr. Biol.* 18, 247-256, 2001). A single N-glycosylation site is conserved in the first large extracellular domain of Glut-2. Black and white circles indicate identical or non-identical amino acids, respectively, among human, rat, and chicken homologues compared to the mouse Glut-2 sequence. (B) Pancreatic islet Glut-2 abundance and lectin binding analysis of Glut-2 N-glycan structure in wild-type and Mgat4a null littermates. (C) Pancreatic islet Glut-2 abundance and lectin blot analysis of N-glycan structure in wild-type and Mgat5 null littermates. (D) Pancreatic islet Glut-2 N-glycan structure deduced from wild-type, Mgat4a null, and Mgat5 null mice. (E) Abundance and lectin binding analysis of N-glycan structures of insulin receptor alpha chain in pancreatic islet cells of wild-type and Mgat4a null littermates. (F) Flow cytometric analyses of pancreatic islet cells for Glut-2 or insulin receptor-alpha subunit expression. Cell auto-fluorescence and secondary antibody non-specific binding are reflected in the two peaks at the left of each panel; cell surface expression and total expression in permeable cells are reflected in the peaks plotted to the right of the backgrounds controls.

Figure 4:
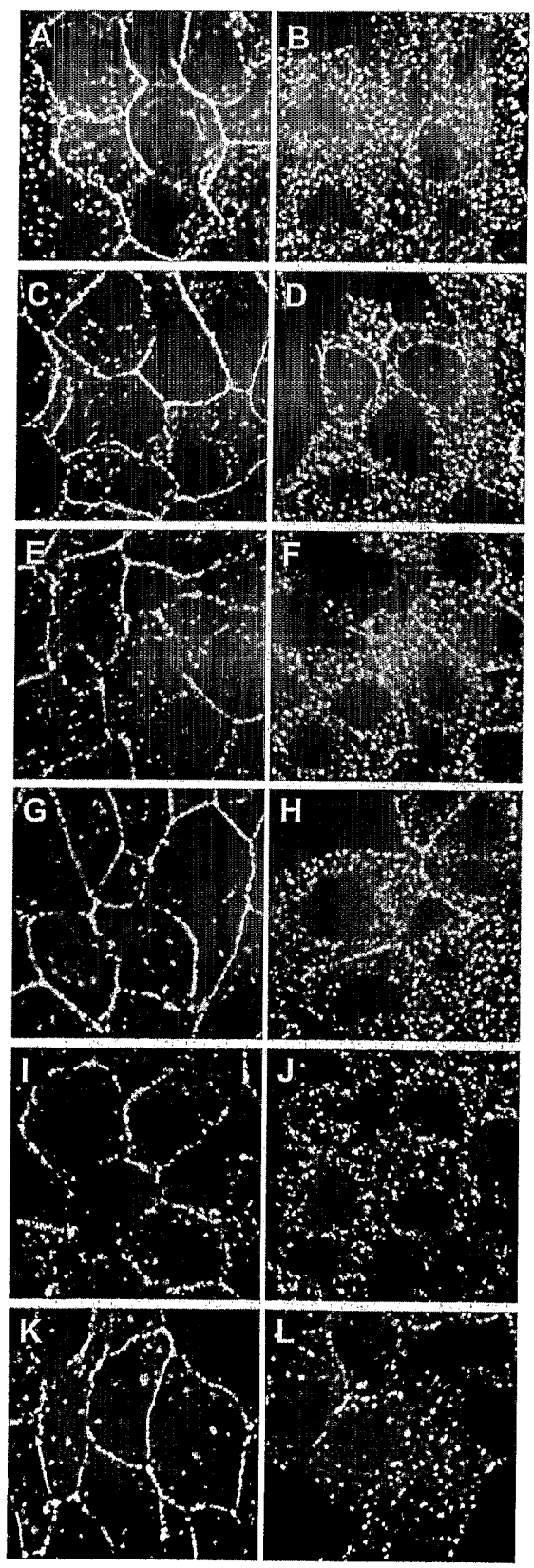

FIG. 4. In-Situ Intracellular Localization of Glut-2 in Pancreatic Beta Cells. Pancreatic islet sections of wild-type (A, C, E, G, I, K) and Mgat4a null (B, D, F, H, J, L) were analyzed by fluorescent and deconvolution microscopy for of Glut-2 expression and various intracellular compartments including secretory vesicular insulin (A, B), endoplasmic reticulum Protein Disulfide Isomerase (C, D), cis-Golgi Calnuc (E, F), trans-Golgi Adaptin-γ (G, H), early endosome antigen EEA-1 (I, J), and lysosome LAMP2 (K, L). DNA is stained by DAPI. Co-localization with Glut-2 is indicated.

Figure 5:
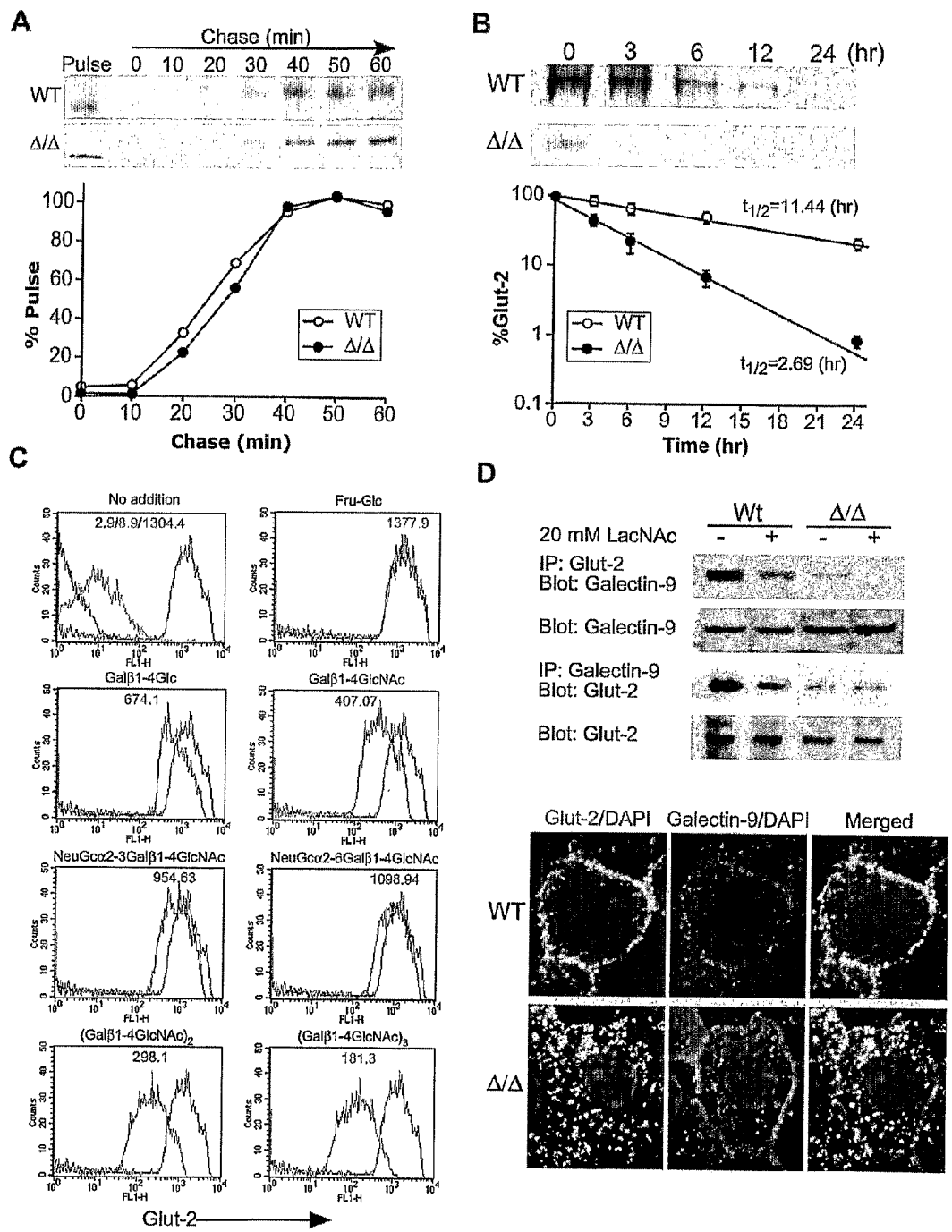

FIG. 5. GnT-4a Glycosylation Promotes Glut-2 Stability at the Cell Surface by a Specific Glycan Binding Mechanism. (A) Production and trafficking of newly synthesized Glut-2 in pancreatic islet cells are normal in GnT-4a deficiency. Intact islet cells were metabolically labeled pulse), then incubated in the absence (chase) of label and their cell surfaces biotinylated at the indicated times. Glut-2 was precipitated from the biotinylated protein fraction and its abundance at various times is graphed as the percent of total (pulse) labeled Glut-2. Thirty-five mice of each genotype were analyzed. (B) Glut-2 cell surface half-life on intact islet cells was measured following cell surface biotinylation at 4° C. and incubation in cell culture conditions at 37° C. for indicated times. Immunoprecipitated Glut-2 was visualized in blots of SDS-PAGE gels using streptavidin-HRP, measured by scanning densitometry, and graphed as a percentage of biotinylated Glut-2 present immediately after biotinylation. Data are represented as the means±S.D. from three separate experiments. (C) Glut-2 expression on the surface of pancreatic islet cells was monitored by flow cytometry following a 2 hr incubation period in cell culture with indicated concentrations of different N-glycan structures. Lactosamine-bearing N-glycans lacking sialic acid termini were specifically able to reduce Glut-2 cell surface expression coincident with increased intracellular binding due to Glut-2 internalization. (D). Protein crosslinking reveals that Glut-2 and URAT/Galectin-9 associate at the cell surface. This association is reduced in Mgat4a deficiency.

Figure 6:
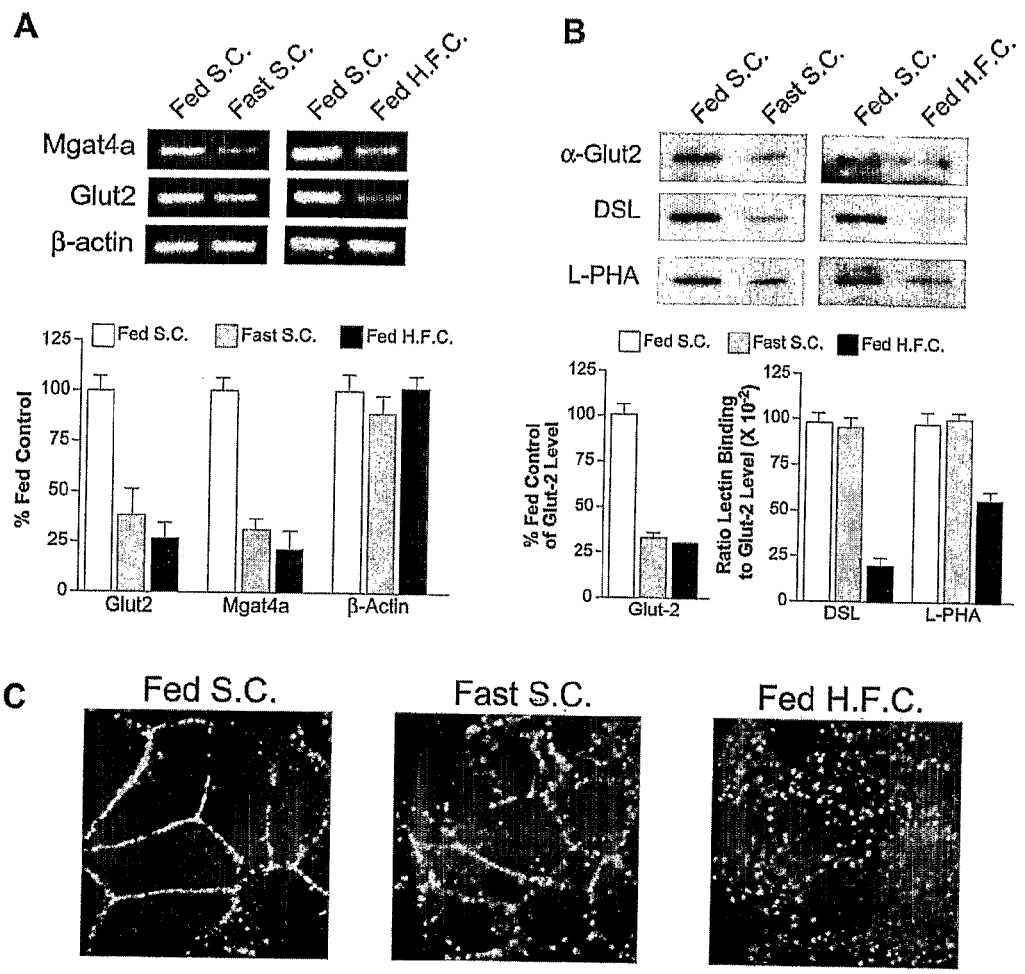

FIG. 6. Dietary Regulation of Pancreatic Mgat4a RNA Abundance, Glut-2 Glycosylation, and Glut-2 Cell Surface Expression. (A) Pancreatic islet Glut-2, Mgat4a, and β-Actin RNA abundance in islets isolated from wild-type mice on standard chow fed ad lib or fasted 48 hrs, and mice on high fat chow ad lib for 8 wks. Total RNA was extracted for RT-PCR. The amplified products were quantified by measuring incorporated $^{32}p$ and graphed as a percent of RNA abundance compared to fed littermates. (B) Glut-2 levels and lectin binding analyses of N-glycan structure in immunoprecipitates of Glut-2 from islets of fed and fasted wild-type mice described in A. Measurements are tabulated as the ratio of lectin binding to the expression level of Glut-2. (C) Glut-2 expression and localization in situ among pancreatic islet sections of mice in the above feeding states visualized with antibodies to Glut-2. DNA is stained by DAPI.

DETAILED DESCRIPTION OF THE INVENTION

Definition

As used herein, "GnT-4" refers to an N-acetylglucosaminyltransferase that initiates the β-4 linked N-acetylglucosamine branch on the α-3 linked core mannose (FIG. 1A) of multiantennary oligosaccharide structures on glycoproteins such as Glut. "GnT-4" refers to both GnT-4a and GnT-4b isozymes. These are well known in the art. Accordingly, "GnT-4 polypeptides" refer to naturally-occurring sequences such as the exemplary sequences provided in SEQ ID NOs:2, 4, 6, or 8, as well as variants or specific fragments of SEQ ID NOs:2, 4, 6, or 8 that have N-acetylglucosaminyltransferase activity. Exemplary human and mouse nucleic acid and protein sequences are provided in SEQ ID NOs:1-8. The sequences of other species, e.g., bovine are also known. A "GnT-4" polypeptide for use in the invention therefore refers to a polypeptide that: (1) has an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a window of at least about 25, 50, 100, 200, or 500, or more amino acids, to a sequence of SEQ ID NO:2 or SEQ ID NO:4; (2) bind to antibodies raised against an immunogen comprising an amino acid sequence of SEQ ID NO:2, SEQ ID NO:4, SEQ ID NO:6, or SEQ ID NO:8; (3) or have at least 15 contiguous amino acids, more often, at least 20, 25, 30, 35, 40, 50 or 100, 200, 300, 400, or 500 contiguous amino acids, of SEQ ID NO:2, SEQ ID NO:4, SEQ ID NO:6, or SEQ ID NO:8.

A "Glucose transporter" or a "Glut" polypeptide or polynucleotide refers to a family of glucose transporters that comprises at least twelve members. These fall into subfamilies based on sequence similarities. Glut 1-4 are in one subfamily (see, e.g., Olson & Pessin, *Ann. Rev. Nutr.* 16, 235-256, 1996; Joost & Thorens, *Mol. Membr. Biol.* 18, 247-256, 2001; and Uldry & Thorens, *Pflugers Arch.* 2004 February; 447(5):480-9, 2004). These proteins all contain twelve transmembrane domains with both the amino and carboxy-terminal ends located on the cytoplasmic side of the plasma membrane and a N-linked oligosaccharide side-chain located either on the first or fifth extracellular loop, the position of that site can be different among subfamilies. Subclass-specific signature sequences are known, see, e.g., Joost & Thorens, supra. As appreciated by those in the art, although these molecules are referred to as glucose transporters, some have additional preferences, such as in the transport of sugars, including mannose, galactose, fructose, and glucosamine.

The following abbreviations are used herein:
Gal=galactosyl;
GlcNAc=N-acetylglucosyl;
Man=mannosyl.

Oligosaccharides are considered to have a reducing end and a non-reducing end, whether or not the saccharide at the reducing end is in fact a reducing sugar. In accordance with accepted nomenclature, oligosaccharides are depicted herein with the non-reducing end on the left and the reducing end on the right.

All oligosaccharides described herein are described with the name or abbreviation for the non-reducing saccharide (e.g., Gal), followed by the configuration of the glycosidic bond (α or β), the ring position of the reducing saccharide involved in the bond, and then the name or abbreviation of the reducing saccharide (e.g., GlcNAc). The linkage between two sugars may be expressed, for example, as Galβ4GlcNac. Each saccharide is a pyranose. Glycoside linkages described herein are assumed to originate form the C1 hydroxyl group except for sialic acids, which are linked form the C2 hydroxyl.

As used herein, "Galβ4GlcNAcβ4Man", or "Galβ4GlcNAcβ4Man branch" refers to the branch of the complex oligosaccharide structure depicted in FIG. 1A that has a Gal in β 1, 4 linkage to GlcNAc, which is in β 1, 4 linkage to the α-3 linked core mannose.

A person is "predisposed for diabetes" when the person is at high risk for developing diabetes. A number of risk factors are known to those of skill in the art and include: genetic factors (e.g., carrying alleles that result in a higher occurrence of diabetes than in the average population or having parents or siblings with diabetes); overweight (e.g., body mass index (BMI) greater or equal to 25 kg/m$^2$); habitual physical inactivity, race/ethnicity (e.g., African-American, Hispanic-American, Native Americans, Asian-Americans, Pacific Islanders); previously identified impaired fasting glucose or impaired glucose tolerance, hypertension (e.g., greater or equal to 140/90 mmHg in adults); HDL cholesterol greater or equal to 35 mg/dl; triglyceride levels greater or equal to 250 mg/dl; a history of gestational diabetes or delivery of a baby over nine pounds; and/or polycystic ovary syndrome. See, e.g., "Report of the Expert Committee on the Diagnosis and Classification of Diabetes Mellitus" and "Screening for Diabetes" *Diabetes Care* 25(1): S5-S24 (2002).

A "pre-diabetic individual" refers to an adult with a fasting blood glucose level greater than 110 mg/dl but less than 126 mg/dl or a 2 hour PG reading of greater than 140 mg/dl but less than 200 mg/dl. A "diabetic individual" refers to an adult with a fasting blood glucose level greater than 126 mg/dl or a 2 hour PG reading of greater than 200 mg/dl.

An "activator" or "agonist" in the context of this invention generally refers to an agent that binds to, increases, facilitates, enhances activation, sensitizes or up regulates the stability of a Glut polypeptide, e.g., Glut-2 or Glut-1, at the cell surface, e.g., by enhancing glycosylation. In some embodiments, an "activator" or "agonist" increases the activity or expression of a glycosyltransferase, e.g, GnT-4.

"Inhibitors" or "antagonists" as used herein are generally agents that, e.g., bind to, decrease, prevent, or down regulate the stability of Glut at a cell surface. In particular embodiments, such inhibitors inhibit the activity or expression of a glycosyltransferase, e.g., GnT-4.

"Antibody," as used herein, refers to a polypeptide substantially encoded by an immunoglobulin gene or immunoglobulin genes, or fragments thereof that specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially an Fab with part of the hinge region (see, Paul (Ed.) *Fundamental Immunology*, Third Edition, Raven Press, N.Y. (1993)). While various antibody fragments are defined in terms of the digestion of an intact antibody, one of skill will appreciate that such fragments may be synthesized de novo either chemically or by utilizing recombinant DNA methodology. Thus, the term antibody, as used herein, also includes antibody fragments either produced by the modification of whole antibodies or those synthesized de novo using recombinant DNA methodologies (e.g., single chain Fv, humanized antibodies, chimeric antibodies, etc.).

The term "nucleic acid" or "polynucleotide" refers to deoxyribonucleotides or ribonucleotides and polymers thereof in either single- or double-stranded form. Unless specifically limited, the term encompasses nucleic acids containing known analogues of natural nucleotides that have similar binding properties as the reference nucleic acid. Unless otherwise indicated, a particular nucleic acid sequence also implicitly encompasses conservatively modified variants thereof (e.g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19: 5081 (1991); Ohtsuka et al., *J. Biol. Chem.* 260: 2605-2608 (1985); and Cassol et al. (1992); Rossolini et al., *Mol. Cell. Probes* 8: 91-98 (1994)).

The term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques.

A "heterologous sequence" or a "heterologous nucleic acid", as used herein, is one that originates from a source foreign to the particular host cell, or, if from the same source, is modified from its original form.

A "subsequence" refers to a sequence of nucleic acids or amino acids that comprise a part of a longer sequence of nucleic acids or amino acids (e.g., polypeptide) respectively.

A "recombinant expression cassette" or simply an "expression cassette" is a nucleic acid construct, generated recombinantly or synthetically, with nucleic acid elements that are capable of affecting expression of a structural gene in hosts compatible with such sequences. Expression cassettes include at least promoters and optionally, transcription termination signals as well as other desired sequences that influence gene expression.

The term "isolated" is meant to refer to material which is substantially or essentially free from components which normally accompany the enzyme as found in its native state. Thus, the enzymes of the invention do not include materials normally associated with their in situ environment. Typically, isolated proteins of the invention are at least about 80% pure, usually at least about 90%, and preferably at least about 95% pure as measured by band intensity on a silver stained gel or other method for determining purity. Protein purity or homogeneity can be indicated by a number of means well known in the art, such as polyacrylamide gel electrophoresis of a protein sample, followed by visualization upon staining. For certain purposes high resolution will be needed and HPLC or a similar means for purification utilized.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified in naturally-occurring cells, e.g., hydroxyproline, γ-carboxyglutamate, and O-phosphoserine. Amino acid "analogs" refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but which functions in a manner similar to a naturally occurring amino acid.

Amino acids may be referred to herein by either the commonly known three letter symbols or by the one-letter symbols recommended by the IUPAC-IUB Biochemical Nomenclature Commission. Nucleotides, likewise, may be referred to by their commonly accepted single-letter codes.

With reference to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, *Proteins* (1984)).

"Percentage of sequence identity" is determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The terms "identical" or percent "identity," in the context of two or more nucleic acids or polypeptide sequences, refer to two or more sequences or subsequences that are the same.

The term "substantially identical" refers to two or more sequences that have a specified percentage of amino acid residues or nucleotides that are the same (i.e., 60% identity, optionally 65%, 70%, 75%, 80%, 85%, 90%, or 95% identity over a specified region or over an entire sequence when no region is specified), when compared and aligned for maximum correspondence over a comparison window, or designated region as measured using one of the following sequence comparison algorithms or by manual alignment and visual inspection. Optionally, the identity exists over a region that is at least about 25 nucleotides or amino acids in length, or more preferably over a region that is 50, or 100 to 500 or more nucleotides or amino acids in length.

The present invention provides polynucleotides and polypeptides substantially identical to SEQ ID NOs:1, 3, 5, or 7; and 2, 4, 6, or 8, respectively. Thus, a GnT-4 polypeptide that is substantially identical, e.g., to SEQ ID NO:2 or SEQ ID NO:4 typically has an amino acid sequence that is at least 60% identical, often at least 65%, 70%, 75%, 80%, 85%, or 90% identical; and preferably at least 91%, 92%, 93%, 94%, 95%, 96%, 97%, 98% or 99% identical; to a sequence of SEQ ID NO:2 or SEQ ID NO:4. The percent identity is preferably over a window of at least 50, 100, 200, or 300, or more amino acids, or over the complete length of the sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) *Adv. Appl. Math.* 2: 482c, by the homology alignment algorithm of Needleman and Wunsch (1970) *J. Mol. Biol.* 48: 443, by the search for similarity method of Pearson and Lipman (1988) *Proc. Nat'l. Acad. Sci. USA* 85: 2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Ausubel et al., *Current Protocols in Molecular Biology* (1995 supplement)).

An example of an algorithm that is suitable for determining percent sequence identity and sequence similarity are the BLAST and BLAST 2.0 algorithms, which are described in Altschul et al. (1977) *Nuc. Acids Res.* 25: 3389-3402, and Altschul et al. (1990) *J. Mol. Biol.* 215: 403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89: 10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90: 5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5× SSC, and 1% SDS, incubating at 42° C., or 5× SSC, 1% SDS, incubating at 65° C., with wash in 0.2× SSC, and 0.1% SDS at 55° C., 60° C., or 65° C. Such washes can be performed for 5, 15, 30, 60, 120, or more minutes.

Nucleic acids that do not hybridize to each other under stringent conditions are still substantially identical if the polypeptides that they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1× SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

The phrases "specifically binds to a protein or lectin" or "specifically immunoreactive with", when referring to an antibody, refers to a binding reaction which is determinative of the presence of the protein in the presence of a heterogeneous population of proteins and other biologics. Thus, under designated assay conditions, the specified protein, e.g., Glut, binds preferentially to a binding partner, e.g., a lectin, antibody, or other protein or binding agent, and does not bind in a significant amount to other lectins or other proteins or binding agents present in the sample. With regard to antibodies, specific binding to a protein under such conditions requires an antibody that is selected for its specificity for a particular protein. A variety of immunoassay formats may be used to select antibodies specifically immunoreactive with a particular protein. For example, solid-phase ELISA immunoassays are routinely used to select monoclonal antibodies specifically immunoreactive with a protein. See Harlow and Lane (1988) *Antibodies, A Laboratory Manual*, Cold Spring Harbor Publications, New York, for a description of immunoassay formats and conditions that can be used to determine specific immunoreactivity.

"Inhibitors," "activators," and "modulators" of expression or of activity are used to refer to inhibitory, activating, or modulating molecules, respectively, identified using in vitro and in vivo assays for expression or activity. Samples or assays comprising a polypeptide of interest, e.g., a glycosyltransferase, e.g. GnT-4, that are treated with a potential agonist can be compared to control samples without the agonist to examine the extent of effect. Control samples (untreated with agonists) are assigned a relative activity value of 100%. Activation of the polypeptide is achieved when the polypeptide activity value relative to the control is 110%, optionally 150%, optionally 200, 300%, 400%, 500%, or 1000-3000% or more higher.

Similar methods can be employed where it is desirable to identify inhibitors or antagonist of Glut stability and/or GnT-4 activity. Inhibition is achieved when the activity value relative to the control is less than about 80%, optionally 50% or 25, 10%, 5% or 1%.

DETAILED DESCRIPTION OF THE INVENTION

Introduction

The present invention is based, in part, on the discovery that Gnt-4 is involved in synthesizing an N-glycan branch that stabilizes Glut on the surface of a cell, e.g., a pancreatic islet cell or a cancer cell. In wild-type pancreatic islet cells, Glut-2 is modified with a complex-type N-glycan bearing a tetra-antennary branch structure as exemplified with little or no sialic acid at terminal linkage positions (e.g., FIG. 3D, left). GnT-4 initiates the β-4 linked N-acetylglucosamine branch on the α-3 linked core mannose (FIG. 1A) of Glut, e.g., Glut-2. The branch includes a series of three sugars, Galβ4GlcNAcβ4Man (shown in the shaded branch depicted in FIG. 1A), which participate in lectin binding. Accordingly, the invention provides methods of identifying agents that increase Glut stability by identifying agents that increase the amount of the Galβ4GlcNAcβ4Man branch. Often the agents modulate a glycosyltransferase, e.g., GNT-4, involved in the synthesis of the branch. Such agents can, for examples increase GnT-4 activity or levels, e.g., in pancreatic islet cells. Further, the invention provides methods of increasing the stability of a Glut polypeptide, e.g., Glut-1 or Glut-2, at the surface of a cell, e.g., a pancreatic islet cell. The stability of a Glut polypeptide is increased by increasing the presence of the Galβ4GlcNAcβ4Man-containing branch shown in FIG. 1 on glycosylated Glut polypeptide. For example, glycosylated Glut polypeptide can be increased by administering an agent that increases GnT-4 activity; or by administering an agent that increases the binding affinity of glycosylated Glut for lectin, e.g., Galectin-9.

The invention also provides methods of treating a diabetic or pre-diabetic individual by administering a modulator that increases Glut stability, e.g., Glut-2 or Glut-1 stability. Such agents can, for example, increase the activity or expression of GnT-4 or another enzyme involved in Galβ4GlcNAcβ4Man branch synthesis.

In another aspect, the invention also provides methods of identifying inhibitors of Glut stability or GnT-4 activity or expression. Such inhibitors, can be used for the treatment of cancer, including but not limited to insulinoma or cancer of the breast, prostate, lung, colon, ovary, pancreas, liver, head and neck, or any other type of cancer.

Methods of identifying modulators of glycosyltransferases involved in the synthesis of a Galβ4GlcNAcβ4Man oligosaccharide branch on Glut are exemplifed herein with reference to GnT-4. As understood by those in the art, the same methodology can be employed to identify modulators of other glycosyltransferases, e.g., gactosyltransferase or mannose transferase.

Identification of GnT-4 Modulators

This invention involves routine techniques in the field of recombinant genetics. Basic texts disclosing the general methods of use in this invention include Sambrook et al., *Molecular Cloning, A Laboratory Manual* (3rd ed. 2001); Kriegler, *Gene Transfer and Expression: A Laboratory Manual* (1990); and *Current Protocols in Molecular Biology* (Ausubel et al., eds., 1994-2004)).

Activators of glycosyltransferases, e.g., GnT-4 agonists (i.e., agents that increase activity or expression of GnT-4) are useful for increasing pancreatic glucose transport in individuals with abnormalities in glucose metabolism, including individuals with type 2 diabetes or individuals with insulin resistance (i.e., pre-diabetic individuals) or other conditions in which it is beneficial to regulate glucose transport.

The screening methods described herein can also be used to identify agents that antagonize (i.e., inhibit or reduce) Glut-2 stability and/or glycosyltransferase, e.g, GnT-4, activity. Such agents can be used, e.g., in for the treatment of cancer or other conditions where it may be desirable to decrease Glut glycosylation, e.g., to decrease Glut binding to lectin.

GnT-4 Modulating Agents

GnT-4 modulators can be any small chemical compound, or a biological entity, such as a protein, sugar, nucleic acid or lipid.

A wide variety of methods can be used to identify agents that increase GnT-4 activity or level. Typically, test compounds will be small chemical molecules and/or peptides. Essentially any chemical compound can be used as a potential modulator (e.g., antagonist) in the assays of the invention, although most often compounds that can be dissolved in aqueous or organic (especially DMSO-based) solutions are used. The assays can be designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland) and the like.

In some embodiments, high throughput screening methods involve providing a combinatorial chemical or peptide library containing a large number of potential therapeutic compounds (potential modulator compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37: 487-493 (1991) and Houghton et al., *Nature* 354: 84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90: 6909-6913 (1993)), vinylogous polypeptides (Hagihara et al., *J. Amer. Chem. Soc.* 114: 6568 (1992)), nonpeptidal peptidomimetics with glucose scaffolding (Hirschmann et al., *J. Amer. Chem. Soc.* 114: 9217-9218 (1992)), analogous organic syntheses of small compound libraries (Chen et al., *J. Amer. Chem. Soc.* 116: 2661 (1994)), oligocarbamates (Cho et al., *Science* 261: 1303 (1993)), and/or peptidyl phosphonates (Campbell et al., *J. Org. Chem.* 59: 658 (1994)), nucleic acid libraries (see Ausubel, Berger and Sambrook, all supra), peptide nucleic acid libraries (see, e.g., U.S. Pat. No. 5,539, 083), antibody libraries (see, e.g., Vaughn et al, *Nature Biotechnology*, 14(3): 309-314 (1996) and PCT/US96/10287), carbohydrate libraries (see, e.g., Liang et al., *Science,* 274: 1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. No. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

GnT-4 Polypeptides

GnT-4 sequences are highly conserved. For example, mouse and human GnT-4a polypeptides share greater than 90% sequence identity. Human and bovine GnT4a have 96% sequence identity (see, e.g., Yoshida et al. *Glycobiology* 9: 303-310, 1999).

GnT-4 polypeptides for use in the invention include GnT-4 polypeptides comprising: a naturally-occurring amino acid sequence such as a human GnT-4a or GnT-4b (e.g., SEQ ID NO:2 or 4), or other animal ortholog, e.g., mouse GnT-4a or GnT-4b (SEQ NO:6 or SEQ ID NO:8). Other naturally occurring variants (relative to the exemplary sequences provided herein, such as bovine GnT-4); or engineered GnT-4 polypeptides can also be employed. Glycosyltransferase structure, including GnT-4 structure, has been well characterized in the art and much is known about the function of such enzymes (see, e.g., the further discussion herein relating to inhibitors of glycosyltransferases). Accordingly, substantial information is available to those of skill in identifying and/or generating such variant GnT-4 polypeptides.

GnT-4 polypeptide variants for use in the invention can be tested, e.g., by assessing the ability of the polypeptide to initiate β-4 linked N-acetylglucosamine branch synthesis, e.g., on a Glut polypeptide such as, Glut-2. Such GnT-4 polypeptides can then be used in assays to identify modulators of GnT-4 activity.

Methods of Screening for Modulators of GnT-4.

A number of different screening protocols can be utilized to identify agents that modulate the activity of GnT-4

Screening can be performed using isolated, purified or partially purified reagents. In some embodiments, purified or partially purified GnT-4 (e.g., cell fractions comprising GnT-4) can be used.

Alternatively, cell-based methods of screening can be used. For example, cells that naturally-express GnT-4 or that recombinantly express GnT-4 can be used. In some embodiments, the cells used are mammalian cells, including but not limited to, human cells. In general terms, the screening methods involve screening a plurality of agents to identify an agent that modulates the activity of GnT-4 by, e.g., binding to and/or increasing or inhibiting the activity of a GnT-4 polypeptide, preventing an inhibitor or activator from binding to GnT-4, increasing association of an inhibitor or activator with GnT-4, or activating or inhibiting expression of GnT-4.

GnT-4 Binding Assays

Optionally, preliminary screens can be conducted by screening for agents that bind to GnT-4. Binding assays are also useful, e.g., for identifying endogenous, or other proteins, that interact with GnT-4. For example, antibodies or other molecules that bind GnT-4 can be identified in binding assays. Such antibodies have use, e.g., as diagnostic agents.

Binding assays usually involve contacting a GnT-4 protein with one or more test agents and allowing the GnT-4 protein and test agent(s) to form a binding complex. Binding complexes that are formed can be detected using any of a number of established analytical techniques. Protein binding assays include, but are not limited to, methods that measure co-precipitation or co-migration on non-denaturing SDS-polyacrylamide gels, and co-migration on Western blots (see, e.g., Bennet, J. P. and Yamamura, H. I. (1985) "Neurotransmitter, Hormone or Drug Receptor Binding Methods," in *Neurotransmitter Receptor Binding* (Yamamura, H. I., et al., eds.), pp. 61-89. Other binding assays involve the use of mass spectrometry or NMR techniques to identify molecules bound to GnT-4 or displacement of labeled substrates. The GnT-4 protein utilized in such assays can be naturally expressed, cloned or synthesized.

In addition, mammalian or yeast two-hybrid approaches (see, e.g., Bartel, P. L. et. al. *Methods Enzymol,* 254: 241 (1995)) can be used to identify polypeptides or other molecules that interact or bind when expressed together in a cell.

GnT-4 Activity

GnT-4 modulators can be identified by screening for agents that alter an activity of GnT-4. Analysis of GnT-4r activity is performed according to general biochemical procedures. Such assays include cell-based assays as well as in vitro assays involving purified or partially purified GnT-4 polypeptides or cellular fractions comprising GnT-4.

In some embodiments, GnT-4 modulators are identified by screening a plurality of agents (generally in parallel) for the ability to GnT-4 activity. The level of GnT-4 activity in a cell or other sample can be determined and compared to a baseline value (e.g., a control value or the GnT-4 activity in a sample not contacted with an agent or the GnT-4 activity in a sample contacted to a different agent).

GnT-4 initiates the β-4 linked N-acetylglucosamine branch on the α-3 linked core mannose of Glut polypeptides such as Glut-2 or Glut-1. Thus, GnT-4 activity can be determined using any number of direct and indirect indicators of activity. For example the transferase activity can be determined directly (e.g., using the guidance provided in the enzymology method section of the Examples). Alternatively, the level of glycosylation can be determined indirectly, typically by measuring the level of lectin binding, e.g., Glut lectin binding. Any lectin that binds to the glycosylated Glut can be used. In preferred embodiment, the lectin binds to the Galβ4GlcNacB4Man oligosaccharide branch. Such lectins include, galectin-9 or a lectin that has a similar oligosaccharide binding specificity, e.g, DSL lectin.

In other embodiments, the level of Glut glycosylation can be reflected by assessing the amount of Glut polypeptide that is stabilized at the cell surface. Accordingly, cell surface-associated Glut polypeptide can be assessed, e.g., by immunoassay, to determine the Glut glycosylation and modulation of GnT-4.

In some embodiments, cells transiently transfected with GnT-4 are measured for GnT-4 activity in suspension or adhered to the plate, within an isotonic buffer. The cells are then contacted to one or more agents and tested for GnT-4 activity.

Screening methods to identify modulators of GnT-4 activity typically employ in at least one of the steps, an assay that uses a GnT-4 polypeptide.

Expression Assays

Screening methods for a compound that modulates the expression of GnT-4 are also provided. Screening methods generally involve conducting cell-based assays in which test compounds are contacted with one or more cells expressing GnT-4, and then detecting an increase or decrease in GnT-4 expression (either transcript, translation product). Assays can be performed with cells that naturally express GnT-4 or in cells recombinantly altered to express a GnT-4.

GnT-4 expression can be detected in a number of different ways. For example, the expression level of GnT-4 in a cell can be determined by evaluating mRNA expression using known methods, e.g., northern blot analysis, in situ hybridization and the like. Alternatively, GnT-4 protein can be detected, e.g., using immunological methods, such as ELISA, immunoblotting, immunoprecipiations, and other well-known techniques.

Other cell-based assays involve reporter assays conducted with cells using standard reporter gene assays. These assays can be performed in either cells that do, or do not, express GnT-4 Some of these assays are conducted with a heterologous nucleic acid construct that includes a comprises a GnT-4 promoter that is operably linked to a reporter gene that encodes a detectable product. A number of different reporter genes can be utilized, including, green fluorescent protein, and enzyme reporters such as β-glucuronidase, CAT (chloramphenicol acetyl transferase; Alton and Vapnek (1979) *Nature* 282: 864-869), luciferase, β-galactosidase and alkaline phosphatase (Toh, et al. (1980) *Eur. J. Biochem.* 182: 231-238; and Hall et al. (1983) *J. Mol. Appl. Gen.* 2: 101).

In these assays, cells harboring the reporter construct are contacted with a test compound. Modulated promoter expression is monitored by detecting the level of a detectable reporter. A number of different kinds of GnT-4 modulators can be identified in this assay. For example, a test compound that activates the promoter by binding to it, or by binding to and activating a transcription factor that binds to the promoter, or by inducing a cascade that produces a molecule that activates the promoter, or that otherwise activates the promoter can be identified. Similarly, a test compound that, e.g., inhibits the promoter by binding to it, or by binding to a transcription factors or other regulatory factor that results in inhibiting the promoter can also be identified.

The level of expression or activity can be compared to a baseline value. The baseline value can be a value for a control sample or a statistical value that is representative of GnT-4 expression levels for a control population (e.g., individuals not having or at risk for Type 2 diabetes) or cells (e.g., tissue culture cells not exposed to a GnT-4 agonist or antagonist). Expression levels can also be determined for cells that do not express a GnT-4 as a negative control. Such cells generally are otherwise substantially genetically the same as the test cells.

Various controls can be conducted to ensure that an observed activity is authentic including running parallel reactions with cells that lack the reporter construct or by not contacting a cell harboring the reporter construct with test compound.

Computer-Based Assays

Other assays for compounds that modulate the activity of GnT-4 involves computer-assisted drug design, in which a computer system is used to generate a three-dimensional structure of GnT-4 based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions (e.g., the active site) of the structure that have the ability to bind ligands or otherwise be modulated. . These regions are then used to identify polypeptides that bind to GnT-4.

Once the tertiary structure of a protein of interest has been generated, potential modulators can be identified by the computer system. Three-dimensional structures for potential modulators are generated by entering chemical formulas of compounds. The three-dimensional structure of the potential modulator is then compared to that of GnT-4 to identify potential modulator binding sites on GnT-4. Binding affinity between the protein and modulators is determined using energy terms to determine which ligands have an enhanced probability of binding to the protein.

Glut-2 Stabilization

In some embodiments, agents that increase Glut stabilization at a cell surface, e.g., a pancreatic islet cell, can be identified using the methods described herein in the section relating to assays for determining GnT-4 activity. Such agents, do not necessarily increase glycosyl transferase activity, e.g., GnT-4 activity, per se, but may, e.g., increase the affinity of Glut for a lectin, e.g., Galectin-9 or a similar lectin. Candidate agents include antibodies, e.g., bivalent antibodies, or small organic molecules.

Similarly, agents that decrease Glut stabilization, e.g., by decreasing Glut-lectin binding can also be screened in activity assays. Such agents, e.g., antibodies or small organic molecule can then be validated in assays that measure inhibition of glucose transport and/or cancer cell growth using assays well known in the art.

Validation of Candidate Modulators

Agents that are initially identified by any of the foregoing screening methods can be further tested to validate the apparent activity and/or determine other biological effects of the agent. In some cases, the identified agent is tested for the ability to alter glucose transport in an animal and/or to alter blood chemistry in a test animal.

In vitro assays using isolated islet cells (normal or diabetic) can be performed in the presence or absence of the candidate activator. In some embodiments, validation studies are conducted with suitable animal models. The basic format of such methods involves administering a lead compound identified during an initial screen to an animal that serves as a model for humans and then determining if GnT-4 activity and/or Glut expression and activity, e.g., lectin binding, transport activity and the like, is in fact modulated following administration of the GnT-4 modulator. The animal models utilized in validation studies generally are mammals of any kind. Specific examples of suitable animals include, but are not limited to, primates, mice and rats. For example, monogenic models of diabetes (e.g., ob/ob and db/db mice, Zucker rats and Zucker Diabetic Fatty (ZDF) rats etc.) or polygenic models of diabetes (e.g., a high fat fed mouse model) can be useful for validating GnT-4 modulation and its effect in a diabetic animal.

Inhibitors of Glycosyltransferases

In some embodiments, e.g., to inhibit cancer cell growth, it may be desirable to reduce Glut stability by inhibiting glycosyltransferase polypeptides, e.g., Gnt-4 polypeptides, that synthesize the complex oligosaccharide shown in FIG. 1A. Preferably, the glycosyltransferases are involved in the synthesis of the shaded branch shown in FIG. 1A, i.e., the Galβ4GlcNAcβ4Man branch.

Preferably, the inhibitor is specific for the particular glycosyltransferase of interest, and the glycosyltransferase is one that is not required for synthesis of other oligosaccharides that are not involved in Glut stabilization. In preferred embodiments, the target glycosyltransferase is a GnT-4.

Having identified the target enzyme to be inhibited (e.g., GnT-4), many approaches can be used to block its activity. Examples of agents capable of inhibiting enzyme activity include immunoglobulins, suicide substrates, alkylating agents, and various substrate analogs. For a review, see Fersht, *Enzyme Structure and Mechanism* (2d ed. 1985). The methods of modulating immune responses by inhibiting glycosyltransferase activity, e.g., GnT4 activity, can involve administering to a mammal a compound that is an analog of a substrate for the glycosyltransferase.

In some embodiments, the inhibitor is a sugar nucleotide or an analog of a donor substrate, e.g., an analog of GlucNAc. The donor substrate of glycosyltransferases are sugar nucleotides, usually diphosphonucleosides. For example, uridine diphosphosugars are donor substrates for the formation of glycosides of glucose, galactose, N-acetylglucosamine, xylose, and glucuronic acid. Guanosine diphosphosugars are donor substrates for the synthesis of glycosides of mannose and fucose. The glycosides of the sialic acids are formed by transfer from cytidine monophosphosialic acid.

Using this knowledge, one of skill in the art can readily synthesize a number of sugar nucleotides which can then be tested to identify those capable of maximum inhibition of a specific enzyme. The term "sugar nucleotide" as used herein refers both to sugar nucleotides discussed above and to various analogs thereof that might be synthesized or isolated from natural sources. The number of variations on this structure is limitless. For instance, both the ester linkage between the sugar and phosphate and the anhydride linkage of the pyrophosphate are potential targets of enzymatic cleavage. Replacement of the O-P or C-O linkage with a more stable C-P bond provides nucleotide monophosphate or diphosphate sugar analogs that are more resistant to enzymatic degradation. Such compounds have the potential to selectively inhibit glycoprotein or glycolipid synthesis by acting as substrate analogs of a particular glycosyltransferase. See, e.g., Vaghefi, et al., *J. Med. Chem.* 30: 1383-1391 (1987), and Vaghefi et al., *J. Med. Chem.* 30: 1391-1399 (1987). Glycosyltransferase inhibitors are also described, for example, in U.S. Pat. No. 5,461,143.

Another approach is to replace the monophosphate or diphosphate bridge between the sugar residue and the nucleoside moiety. For instance, the diphosphate bridge can be replaced with an isosteric —OCONHSO$_2$O— residue. See, Samarasa, et al., *J. Med. Chem.* 28: 40-46 (1985).

Analogs of sugar nucleotides capable of inhibiting glycosylation have been used as antibiotics and antiviral agents. Examples of such compounds include 2-deoxy-D-glucose, which is transformed to either UDP-2dGlc or GDP-2dGlc and in that form inhibits glycosylation of glycoproteins in the viral envelope. DeClercq, *Biochem. J.* 205:1 (1982) which is incorporated herein by reference. Antibiotics such as tunicamycin and streptovirudin are also effective because of their ability to inhibit glycosylation. For instance, tunicamycin is an analog of UDP-GlcNAc, the donor substrate for N-acetyl-glucos-aminyltransferases. The replacement of diphosphate bridge with a carbon chain allows tunicamycin to cross the cell membrane but still readily bind the active site of the enzyme. The structure of these and related compounds provide one of skill in the art with direction in designing and synthesizing compounds with similar inhibitory effects in accordance with the present invention as described herein. Additional analogs of sialic acid sugar nucleotides that are useful in the methods of the invention include, for example CMP-quinic acid and derivatives thereof (Schaub et al. (1998) *Glycoconjugate J.* 15: 345-354).

Nucleotides are the byproduct of the reaction by which glycosyl residues are transferred to acceptor substrates. Nucleotides have been found to competitively inhibit glycosyltransferase. Thus, various nucleotides and their analogs have potential as inhibitors of these enzymes.

In addition to the donor substrate analogs, analogs of acceptor substrates may also be used as inhibitors. Again, the skilled artisan will recognize a variety of possible structures that can be used. Ideally, the inhibitory compounds should be capable of acting as specific acceptor substrates for a given enzyme, even in the presence of other enzymes. In addition, the compound should be an efficient acceptor substrate. Thus, the $K_i$ of the inhibitor should be at least about $10^{-5}$ M, more preferably at least about $10^{-7}$ M.

Glycosyltransferases can also be inhibited by contacting acceptor substrates for the glycosyltransferase with a competing glycosyltransferase or glycosidase that converts the acceptor oligosaccharide into a different structure that does not function as an acceptor for the glycosyltransferase of interest.

The preferred glycosyltransferase inhibitors of the present invention have the ability to cross the cell membrane and enter the Golgi apparatus. Thus, the blocking agents are preferably sufficiently hydrophobic to allow diffusion through the membrane. Generally, they have no other adverse effects on cellular metabolism, so that other glycosylation reactions proceed while the specific reaction is inhibited. The blocking agents are preferably relatively small molecules, thereby avoiding immunogenicity and allowing passage through the cell membrane. Ideally, they have a molecular weight of between about 100-2000 daltons, but may have molecular weights up to 5000 or more, depending upon the desired application. In most preferred embodiments, the inhibitors have molecular weights of between about 200-600 daltons.

The inhibitors of the present invention preferably have strong affinity for the target enzyme, so that at least about 70% inhibition of glycosyltransferase activity is typically achieved, more preferably about 75%-85% and most preferably 90%-95% or more. The affinity of the enzyme for the inhibitor is preferably sufficiently strong that the dissociation constant, or $K_i$, of the enzyme-inhibitor complex is less than about $10^{-5}$ M, typically between about $10^{-6}$ and $10^{-8}$ M.

Enzyme inhibition generally involves the interaction of a substance with an enzyme so as to decrease the rate of the reaction catalyzed by that enzyme. Inhibitors can be classified according a number of criteria. For example, they may be reversible or irreversible. An irreversible inhibitor dissociates very slowly, if at all, from its target enzyme because it becomes very tightly bound to the enzyme, either covalently or noncovalently. Reversible inhibition, in contrast, involves an enzyme-inhibitor complex which may dissociate.

Inhibitors can also be classified according to whether they are competitive, noncompetitive or uncompetitive inhibitors. In competitive inhibition for kinetically simple systems involving a single substrate, the enzyme can bind either the substrate or the inhibitor, but not both. Typically, competitive inhibitors resemble the substrate or the product(s) and bind the active site of the enzyme, thus blocking the substrate from binding the active site. A competitive inhibitor diminishes the rate of catalysis by effectively reducing the affinity of the substrate for the enzyme. Typically, an enzyme may be competitively inhibited by its own product because of equilibrium considerations. Since the enzyme is a catalyst, it is in principle capable of accelerating a reaction in the forward or reverse direction.

Noncompetitive inhibitors allow the enzyme to bind the substrate at the same time it binds the inhibitor. A noncompetitive inhibitor acts by decreasing the turnover number of an enzyme rather than diminishing the proportion of free enzyme. Another possible category of inhibition is mixed or uncompetitive inhibition, in which the inhibitor affects the binding site and also alters the turnover number of the enzyme. Enzyme inhibition of kinetically complex systems involving more than one substrate, as is the case for glycosyltransferases, are described in Segel, *Enzyme Kinetics*, (Wiley, N.Y. 1975).

In vitro and/or in vivo assays can o be used to validate inhibitor activity. Such assays typically employ cancer cells and assess the ability to decrease glucose transport in cancer cells and inhibit cancer cell growth. Such assays are well known in the art.

Administration And Pharmaceutical Compositions

Modulators of glycosyltransferases involved in Galβ-GlcNAcβMan branch synthesis, e.g., GnT-4 (e.g., GnT-4 agonists) can be administered directly to the mammalian subject in need thereof for modulation of GnT-4 activity in vivo. Individuals in need of activators of glycosyltransferases involved in GalβGlcNAcβMan branch synthesis, e.g, GnT-4, can include, for example, individuals with type 2 diabetes, pre-diabetic individuals, or individuals having other abnormalities of glucose metabolism. Individuals in need of inhibitors of glycosyltransferases involved in GalβGlcNAcβMan branch synthesis, e.g., GnT-4, include cancer patients, including those with insulinoma or other cancers. Administration is by any of the routes normally used for introducing a modulator compound into ultimate contact with the tissue to be treated and is well known to those of skill in the art. Although more than one route can be used to administer a particular composition, a particular route can often provide a more immediate and more effective reaction than another route.

The pharmaceutical compositions of the invention may comprise a pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, 17$^{th}$ ed. 1985)).

Modulators, e.g., agonists, alone or in combination with other suitable components, can be prepared for injection or for use in a pump device. Pump devices (also known as "insulin pumps") are commonly used to administer insulin to patients and therefore can be easily adapted to include compositions of the present invention. Manufacturers of insulin pumps include Animas, Disetronic and MiniMed.

Modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and non-aqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, or intrathecally. The formulations of compounds can be presented in unit-dose or multi-dose sealed containers, such as ampoules and vials. Solutions and suspensions can be prepared from sterile powders, granules, and tablets of the kind previously described. The modulators can also be administered as part of a prepared food or drug.

The dose administered to a patient, in the context of the present invention should be sufficient to induce a beneficial response in the subject over time. The optimal dose level for any patient will depend on a variety of factors including the efficacy of the specific modulator employed, the age, body weight, physical activity, and diet of the patient, on a possible combination with other drugs, and on the severity of the case of diabetes. It is recommended that the daily dosage of the modulator be determined for each individual patient by those skilled in the art in a similar way as for known insulin compositions. The size of the dose also will be determined by the existence, nature, and extent of any adverse side-effects that accompany the administration of a particular compound or vector in a particular subject.

In determining the effective amount of the modulator to be administered a physician may evaluate circulating plasma levels of the modulator, modulator toxicity, and the production of anti-modulator antibodies. In general, the dose equivalent of a modulator is from about 1 ng/kg to 10 mg/kg for a typical subject.

For administration, glycosyltransferase modulators, e.g, GnT-4 modulators, can be administered at a rate determined by the LD-50 of the modulator, and the side-effects of the modulator at various concentrations, as applied to the mass and overall health of the subject. Administration can be accomplished via single or divided doses.

The compounds of the present invention can also be used effectively in combination with one or more additional active agents depending on the desired target therapy (see, e.g., Turner, N. et al. *Prog. Drug Res.* (1998) 51: 33-94; Haffner, S. *Diabetes Care* (1998) 21: 160-178; and DeFronzo, R. et al. (eds.), *Diabetes Reviews* (1997) Vol. 5 No. 4). A number of studies have investigated the benefits of combination therapies with oral agents (see, e.g., Mahler, R., *J. Clin. Endocrinol. Metab.* (1999) 84: 1165-71; United Kingdom Prospective Diabetes Study Group: UKPDS 28, *Diabetes Care* (1998) 21: 87-92; Bardin, C. W.,(ed.), *Current Therapy In Endocrinology And Metabolism,* 6th Edition (Mosby - Year Book, Inc., St. Louis, Mo. 1997); Chiasson, J. et al., *Ann. Intern. Med.* (1994) 121: 928-935; Coniff, R. et al., *Clin. Ther*. (1997) 19: 16-26; Coniff, R. et al., *Am. J. Med*. (1995) 98: 443-451; and Iwamoto, Y. et al., *Diabet. Med.* (1996) 13 365-370; Kwiterovich, P. *Am. J. Cardiol* (1998) 82(12A): 3U-17U). These studies indicate that modulation of diabetes, among other diseases, can be further improved by the addition of a second agent to the therapeutic regimen. Combination therapy includes administration of a single pharmaceutical dosage formulation that contains a GnT-4 modulator of the invention and one or more additional active agents, as well as administration of a GnT-4 modulator and each active agent in its own separate pharmaceutical dosage formulation. For example, a GnT-4 modulator and a thiazolidinedione can be administered to the human subject together in a single oral dosage composition, such as a tablet or capsule, or each agent can be administered in separate oral dosage formulations. Where separate dosage formulations are used, a GnT-4 modulator and one or more additional active agents can be administered at essentially the same time (i.e., concurrently), or at separately staggered times (i.e., sequentially). Combination therapy is understood to include all these regimens.

One example of combination therapy can be seen in modulating diabetes (or treating diabetes and its related symptoms, complications, and disorders), wherein the GnT-4 modulators can be effectively used in combination with, for example, sulfonylureas (such as chlorpropamide, tolbutamide, acetohexamide, tolazamide, glyburide, gliclazide, glynase, glimepiride, and glipizide); biguanides (such as metformin); a PPAR beta delta agonist; a ligand or agonist of PPAR gamma such as thiazolidinediones (such as ciglitazone, pioglitazone (see, e.g., U.S. Pat. No. 6,218,409), troglitazone, and rosiglitazone (see, e.g., U.S. Pat. No.5,859,037)); PPAR alpha agonists such as clofibrate, gemfibrozil, fenofibrate, ciprofibrate, and bezafibrate; dehydroepiandrosterone (also referred to as DHEA or its conjugated sulphate ester, DHEA-SO4); anti-glucocorticoids; TNFα inhibitors; α-glucosidase inhibitors (such as acarbose, miglitol, and voglibose); amylin and amylin derivatives (such as pramlintide, (see, also, U.S. Pat. Nos.

5,902,726; 5,124,314; 5,175,145 and 6,143,718.)); insulin secretogogues (such as repaglinide, gliquidone, and nateglinide (see, also, U.S. Pat. Nos. 6,251,856; 6,251,865; 6,221,633; 6,174,856)), and insulin.

Pharmaceutically acceptable carriers are determined in part by the particular composition being administered, as well as by the particular method used to administer the composition. Accordingly, there is a wide variety of suitable formulations of pharmaceutical compositions of the present invention, as described below (see, e.g., *Remington's Pharmaceutical Sciences*, 17th ed., 1989).

In some embodiments, sialyltransferase inhibitos can be administerd to enhance pancreatic Glut stabilization. These embodiments relate to conditions in which sialyltransferase in the pancreas leads to increased levels of sialic acid at the terminal positions of the complex carbohydrate shown in FIG. 1A, thus destabilizing Glut at the surface of pancreatic cells.

Administration of Nucleic Acid Modulators

Conventional viral and non-viral based gene transfer methods can be used to introduce nucleic acids encoding a glycosyltransferase involved in GalβGlcNAcβMan branch synthesis, e.g., GnT-4, to target tissues, in particular pancreatic tissue or stem cells. Such methods can be used to administer nucleic acids encoding polypeptides of the invention to cells in vitro. In some embodiments, the nucleic acids encoding polypeptides of the invention are administered for in vivo or ex vivo gene therapy uses. Non-viral vector delivery systems include DNA plasmids, naked nucleic acid, and nucleic acid complexed with a delivery vehicle such as a liposome. Viral vector delivery systems include DNA and RNA viruses, which have either episomal or integrated genomes after delivery to the cell. For a review of gene therapy procedures, see Anderson, *Science* 256: 808-813 (1992); Nabel & Felgner, *TIBTECH* 11: 211-217 (1993); Mitani & Caskey, *TIBTECH* 11: 162-166 (1993); Dillon, *TIBTECH* 11: 167-175 (1993); Miller, *Nature* 357: 455-460 (1992); Van Brunt, *Biotechnology* 6(10): 1149-1154 (1988); Vigne, *Restorative Neurology and Neuroscience* 8: 35-36 (1995); Kremer & Perricaudet, *British Medical Bulletin* 51(1): 31-44 (1995); Haddada et al., in *Current Topics in Microbiology and Immunology* Doerfler and Böhm (eds) (1995); and Yu et al., *Gene Therapy* 1: 13-26 (1994).

Methods of non-viral delivery of nucleic acids encoding engineered polypeptides of the invention include lipofection, microinjection, biolistics, virosomes, liposomes, immunoliposomes, polycation or lipid: nucleic acid conjugates, naked DNA, artificial virions, and agent-enhanced uptake of DNA. Lipofection is described in e.g., U.S. Pat. No. 5,049,386, U.S. Pat. No. 4,946,787; and U.S. Pat. No. 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid: nucleic acid complexes, including targeted liposomes such as immunolipid complexes, is well known to one of skill in the art (see, e.g., Crystal, *Science* 270: 404-410 (1995); Blaese et al., *Cancer Gene Ther.* 2: 291-297 (1995); Behr et al., *Bioconjugate Chem.* 5: 382-389 (1994); Remy et al., *Bioconjugate Chem.* 5: 647-654 (1994); Gao et al., *Gene Therapy* 2: 710-722 (1995); Abmad et al., *Cancer Res.* 52: 4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding polypeptides of the invention take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of polypeptides of the invention could include retroviral, lentivirus, adenoviral, adeno-associated and herpes simplex virus vectors for gene transfer. Viral vectors are currently the most efficient and versatile method of gene transfer in target cells and tissues. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In some embodiments, cells are isolated from the subject organism, transfected with a nucleic acid (gene or cDNA) encoding a polypeptides of the invention, and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, e.g., pancreatic tissue Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and Iad (differentiated antigen presenting cells) (see Inaba et al., *J. Exp. Med.* 176: 1693-1702 (1992)).

In other embodiments, nucleic acids encoding glycosyltransferases, e.g., GnT-4, can be introduced into pancreatic islet cells ex vivo and then reintroduced into the patient.

Vectors (e.g., retroviruses, adenoviruses, liposomes, etc.) containing therapeutic nucleic acids can also be administered directly to the organism for transduction of cells in vivo. Alternatively, naked DNA can be administered. Administration is by any of the routes normally used for introducing a molecule into ultimate contact with blood or tissue cells. Suitable methods of administering such nucleic acids are available and well known to those of skill in the art, and, although more than one route can be used to administer a particular composition, a particular route can often provide a more immediate and more effective reaction than another route.

In some embodiments, e.g., administration of inhibitory nucleic acids, e.g., nucleic acid inhibitors of GnT-4, can be used to inhibition growth of cancer cells. An "inhibitory nucleic acid" is any nucleic acid or modified nucleic acid used or designed for use in inhibitory nucleic acid therapy. "Inhibitory nucleic acid therapy" refers to the use of inhibitory nucleic acids to inhibit gene expression, for example, inhibition of DNA transcription, inhibition of RNA processing, transport or translation, or inhibition of protein synthesis. Inhibitory nucleic acid therapy includes the variety of approaches for treatment of disease using nucleic acids or modified nucleic acids as described herein. Various inhibitory nucleic acid therapies are known. For example, nucleic acid inhibitors such as siRNA or antisense molecules are administered. In mammalian cells, introduction of long dsRNA (>30 nt) often initiates a potent antiviral response, exemplified by nonspecific inhibition of protein synthesis and RNA degradation. The phenomenon of RNA interference is described and discussed, e.g., in Bass, Nature 411: 428-29 (2001); Elbahir et al., Nature 411: 494-98 (2001); and Fire et al, Nature 391: 806-11 (1998), where methods of making interfering RNA also are discussed. siRNAs based upon GNT-4 sequences, e.g., the human GnT-4 sequences disclosed herein, are less than 100 base pairs, typically 30 bps or shorter, and are made by approaches known in the art. Exemplary siRNAs according to the invention could have up to 29 bps, 25 bps, 22 bps, 21 bps, 20 bps, 15 bps, 10 bps, 5 bps or any integer thereabout or therebetween.

In some embodiments, sialyltransferase inhibitory nucleic acids can be administerd to enhance pancreatic Glut stabilization. These embodiments relate to conditions in which sialyltransferase in the pancreas leads to increased levels of sialic acid at the terminal positions of the complex carbohydrate shown in FIG. 1, thus destabilizing Glut at the surface of pancreatic cells.

Diagnosis of Risk for Disease

In some embodiments, the invention provides method of diagnosing a risk for diabetes. Risk for diabetes can be assessed for example, by determining the presence of mutations that inhibit the activity of glycosyltransferases involved in Galβ4GlcNAcβ4Man branch synthesis, e.g., GnT-4 transferase. Such mutations can lead to decreased levels of this oligosaccharide branch, and thus, decreased Glut stability, resulting in loss of glucose transporter activity.

In other embodiments, disease risk can be assessed, for example, by determining whether mutations are present in sialyltransferase genes or genes that regulate sialyltransferases that lead to abnormal expression of sialyltransferase in the pancreas. Such changes in expression can result in the presence of increased levels of sialic acid at the terminal positions of the complex oligosaccharide branch shown in FIG. 1A, including the Galβ4GlcNAcβ4Man branch, which thus destabilizes Glut at the cell surface.

EXAMPLES

Example 1

Mutagenesis of the Mgat4a Gene Encoding the GnT-4a Glycosyltransferase

Specifically eliminating GnT-4a activity in vivo began by inactivation of the Mgat4a gene in mouse embryonic stem cells using Cre-loxP mutagenesis (FIG. 1C). Exon 7 was flanked by loxP sites (F, floxed) placed in surrounding introilic sequences and this modification was targeted into embryonic stem cells that were subsequently used to produce mice heterozygous for the Mgat4a$^F$ allele (FIG. 1D). These were bred with mates expressing Cre recombinase in developing oocytes (Shafi et al., 2001) to produce offspring heterozygous and homozygous for the deleted (Δ) Mgat4a$^\Delta$ allele lacking exon 7 (FIG. 1D). Deletion of exon 7 disrupts the catalytic domain of GnT-4a and results in a frameshift followed closely by a translational termination signal in any residual Mgat4a RNA molecules produced. Mutant allele segregation among offspring was normal and animals lacked gross physical, neurological, or reproductive defects. GnT-4a enzymatic activity is normally widespread but highest in the pancreas among tissues of wild-type mice surveyed. Most tissues of mice heterozygous for the Mgat4a$^\Delta$ allele expressed approximately 50% of wild-type enzyme activity levels, while homozygotes lacked significant GnT-4 activity in all tissues including the pancreas, with the exception of the kidney. The profile of remaining GnT-4 activity includes the expression pattern and enzymatic activity levels characteristic of the Mgat4b-encoded GnT-4b isozyme. We conclude that the germline deletion of exon 7 in the mouse Mgat4a gene disables GnT-4a synthesis and eliminates GnT-4a activity in vivo.

Example 2

GnT-4a Deficiency Impairs Glucose Transport and Insulin Secretion in Causing a Syndrome Similar to Human Adult-Onset Type 2 Diabetes Blood chemistry parameters were abnormal in 8-12 week old GnT-4a deficient mice fed ad lib with standard chow (Table 1). Serum glucose levels reached pre-diabetic and diabetic concentrations. Free fatty acid and triglyceride levels were also significantly elevated while serum insulin averaged only 40% of normal. These abnormalities increased in severity as animals reached one year of age and serological evidence of liver damage appeared during this time (Table 1). Although only a minor percentage of GnT-4a deficient mice became obese, by 6-8 months of age they averaged 20% above the body weight of wild-type littermates. Upon being fed a high fat diet for 8 weeks ad lib, elevated glucose levels were present in both wild-type and GnT-4a deficient mice, with GnT-4a deficiency resulting in a more severe increase (Table 1). On the high-fat diet, the average body weight of wild-type mice increased 42% above that of those receiving standard chow while GnT-4a deficient mice underwent a 67% increase.

The pancreas of GnT-4a deficient mice appeared unremarkable upon histologic analysis and without evidence of leukocyte infiltrates (FIG. 2A). The abundance and size of pancreatic islets were normal (FIG. 2B). However, fasted GnT-4a deficient mice exhibited abnormalities in pancreatic function in the glucose tolerance test. Glucose levels increased substantially above the normal response and remained elevated while insulin levels failed to substantially increase (FIG. 2C, D). Insulin insufficiency was not due to a defect of insulin production or the secretory process in general as L-arginine treatment resulted in robust increases in serum insulin concentrations in both wild-type and GnT-4a deficient mice (FIG. 2E). Although insulin sensitivity was normal at 8-12 weeks of age, insulin resistance developed to encompass all GnT-4a deficient animals by one year of age (FIG. 2F, G). During this time, RNA levels encoding liver gluconeogenic enzymes phosphoenolpyruvate carboxykinase (PEPCK) and glucose 6-phosphatase (G6Pase) remained significantly elevated among GnT-4a deficient mice fed ad lib (FIG. 2H). Severe and diffuse hepatic steatosis was observed by 6 months of age among the majority of GnT-4a deficient mice fed ad lib standard chow (FIG. 2I).

Intact and viable pancreatic islet preparations comprising >90% beta cells were isolated and further analyzed. Glucose sensing and insulin secretion were investigated by in vitro perfusion in the presence of increasing concentrations of glucose. As expected, eluates from wild-type islets revealed an acute release of insulin in the primary secretory response with a secondary insulin release response that occurred several minutes later. In contrast, GnT-4a deficient islet cells failed to undergo a primary insulin release response and exhibited a significantly reduced secondary response (FIG. 2J). The kinetics of glucose transport by pancreatic islet cells was analyzed using the fluorescent glucose analog 2-NBDG. Wild-type cells incorporated 2-NBDG in a glucose-dependent manner at a nominal rate, while GnT-4a deficient islet cells were defective in 2-NBDG uptake (FIG. 2K). While the Km for 2-NBDG binding was not altered by GnT-4a deficiency, a substantial decrease in Vmax of approximately 10-fold was apparent (FIG. 2L). These findings suggest a defect in glucose transporter expression resulting in reduced glucose uptake and defective insulin release in GnT-4a deficient pancreatic beta cells.

Example 3

GnT-4a Selectively Promotes Pancreatic Glucose Transporter-2 Abundance and Cell Surface Expression Glucose transporter-2 (Glut-2) is important for glucose uptake and insulin secretion in pancreatic beta cells. Glut-2 structure is highly conserved between avian, rodent, and primate genomes, including the retention of a single N-glycosylation site in the first extracellular loop (FIG. 3A). A significant reduction in Glut-2 protein levels was observed in GnT-4a deficient islet cells averaging 50% of normal. This was associated with a reduction in DSL lectin binding to remaining Glut-2 reflecting the absence of the N-glycan branch formed in the presence of Golgi GnT4 activity (FIG. 3B). Unexpectedly, a separate N-glycan branch contributed by Golgi GnT5 activity and visualized by L-PHA lectin binding was also deficient from the Glut-2 N-glycan produced by Mgat4a null islets (FIG. 3B). We therefore analyzed Glut-2 abundance and structure among Mgat5 null mice lacking GnT-5 activity. No alterations in pancreatic islet Glut-2 abundance or DSL lectin binding were observed; while L-PHA ligands were deficient as expected (FIG. 3C).

Normal and altered structures of the N-glycan on pancreatic islet Glut-2 were deduced from these data and knowledge of vertebrate N-glycan biosynthetic pathways in the Golgi. In wild-type islet cells, Glut-2 is modified with a complex-type N-glycan bearing a tetra-antennary branch structure as exemplified with little or no sialic acid at terminal linkage positions (FIG. 3D, left). Absence of GnT-4a results in a complex-type bi-antennary N-glycan, while GnT5 deficiency results in a complex-type tri-antennary structure (FIG. 3D, middle, right). The loss of GnT-4a activity identically alters N-glycan branching on other pancreatic islet glycoproteins including the alpha subunit of the insulin receptor (IRα) and insulin-like growth factor-2 receptor. Nevertheless, expression levels of these glycoproteins are unaffected by GnT-4a deficiency (FIG. 3E and data not shown).

Pancreatic islet cells were analyzed by flow cytometry using intact and membrane-permeable conditions to quantify total and cell surface glycoprotein expression. Glut-2 and IRα in pancreatic beta cells are normally found at the cell surface and not among intracellular compartments. In addition to the reduced total Glut-2 expression noted above, cell surface expression of Glut-2 was reduced 10-fold on average in GnT-4a deficiency compared with wild-type and Mgat4a$^F$ homozygous cells and coincident with 80% of Glut-2 residing within membrane bound compartments (FIG. 3F). Cells heterozygous for the Mgat4a$^Δ$ allele exhibited a partial phenotype while Mgat5 null cells retained normal Glut-2 expression profiles. None of these genetic lesions affected cell surface and total expression levels of IRα (FIG. 3F).

Example 4

Altered Glut-2 Trafficking and Half-Life at the Cell Surface in GnT-4a Deficiency The in situ location of pancreatic beta cell Glut-2 was investigated using fluorescent and deconvolution microscopy of pancreatic islets with immunological markers of intracellular organelles and compartments. Glut-2 protein trafficking in pancreatic beta cells was dramatically altered by GnT-4a deficiency. Normally Glut-2 expression is broadly disbursed on the plasma membrane in contrast to the predominant intracellular punctate pattern observed in Mgat4a null mice (FIG. 4A, B). Co-localization analyses indicated no significant overlap with insulin secretory vesicles, the endoplasmic reticulum, the cis-Golgi, and the trans-Golgi (FIG. 4A-H). However, Glut-2 expression was increased in early endosomes and lysosomes (FIG. 4I-L).

Glut-2 synthesis, trafficking and half-life at the cell surface were measured among isolated cultured pancreatic islet cells using metabolic labeling coupled with cell surface biotinylation. Glut-2 synthesis and transport to the cell surface occurred with normal kinetics in GnT-4a deficiency (FIG. 5A). However, Glut-2 half-life at the cell surface in the absence of glycosylation by GnT-4a was decreased more than 4-fold from 11.4 to 2.7 hours (FIG. 5B).

TABLE 1

Blood Chemistry

| 8-12 weeks of age standard chow | Wild type (n = 20) | Mgat4a Null (n = 20) |
|---|---|---|
| Glucose (fasting) (mg/dL) | 96.20 ± 6.26 | 137.05 ± 5.68*** |
| Glucose (fed) (mg/dL) | 138.82 ± 6.55 | 193.59 ± 8.99*** |
| Insulin (fasting) (ng/ml) | 0.712 ± 0.048 | 0.633 ± 0.036 |
| Insulin (fed) (ng/ml) | 2.916 ± 0.373 | 1.191 ± 0.105*** |
| Free fatty acid (fasting) | 1.04 ± 0.04 | 1.36 ± 0.12* |
| Free fatty acid (fed) | 0.58 ± 0.06 | 0.58 ± 0.04 |
| Triglyceride (mg/dL) | 47.3 ± 2.02 | 91.70 ± 10.80** |
| AST (IU/L) | 76.36 ± 5.68 | 96.31 ± 11.83 |
| ALT (IU/L) | 24.92 ± 1.03 | 27.85 ± 1.55 |
| Lipase (U/L) | 48.33 ± 2.15 | 44.62 ± 1.75 |
| Total cholesterol (mg/dL) | 94.67 ± 4.76 | 105.12 ± 6.80 |
| HDL-cholesterol (mg/dL) | 79.72 ± 5.56 | 88.94 ± 7.30 |

| 12 months of age standard chow | Wild type (n-15) | Mgat4a Null (n = 15) |
|---|---|---|
| Glucose (fasting) (mg/dL) | 108.9 ± 7.72 | 168.6 ± 10.14*** |
| Glucose (fed) (mg/dL) | 193.2 ± 8.12 | 249.4 ± 15.41** |
| Insulin (fasting) (ng/ml) | 1.023 ± 0.127 | 0.651 ± 0.087*** |
| Insulin (fed) (ng/ml) | 4.389 ± 0.361 | 1.673 ± 0.121*** |
| Free fatty acid (fasting) | 1.10 ± 0.03 | 1.66 ± 0.05*** |
| Free fatty acid (fed) | 0.62 ± 0.06 | 0.68 ± 0.04 |
| Triglyceride (mg/dL) | 102.6 ± 8.93 | 158.5 ± 18.75* |
| AST (IU/L) | 96.52 ± 6.58 | 170.8 ± 14.21*** |
| ALT (IU/L) | 87.39 ± 6.60 | 173.2 ± 10.57*** |
| Lipase (U/L) | 60.63 ± 4.81 | 52.82 ± 3.80 |

TABLE 1-continued

| Blood Chemistry | | |
|---|---|---|
| Total cholesterol (mg/dL) | 190.9 ± 15.00 | 176.6 ± 14.32 |
| HDL-cholesterol (mg/dL) | 168.0 ± 7.84 | 152.0 ± 12.57 |
| 12 weeks of age 8 weeks on high-fat chow | Wild type (n = 14) | Mgat4a Null (n = 14) |
| Glucose (fed) (mg/dL) | 237.4 ± 11.53 | 307.2 ± 10.45*** |
| Insulin (fed) (ng/ml) | 6.617 ± 0.907 | 4.023 ± 0.324* |
| Free fatty acid (fed) | 1.59 ± 0.08 | 1.56 ± 0.06 |
| Triglyceride (mg/dL) | 104.3 ± 8.53 | 98.86 ± 5.53 |
| AST (IU/L) | 100.9 ± 7.19 | 106.0 ± 5.62 |
| ALT (IU/L) | 72.50 ± 9.31 | 84.29 ± 6.87 |
| Lipase (U/L) | 64.50 ± 6.70 | 66.00 ± 7.27 |
| Total cholesterol (mg/dL) | 149.2 ± 10.80 | 171.1 ± 4.70 |
| HDL-cholesterol (mg/dL) | 122.0 ± 8.49 | 117.9 ± 5.96 |

*$p < 0.005$;
**$p < 0.001$;
***$p < 0.0001$

Experimental Methods

Mgat4a Expression and Mutagenesis

Mouse Mgat4a cDNA fragments GT4F7/GT4R6 and GT4F3/GB5, were obtained by RT-PCR using primers, GT4F7: 5'-atgaggctccgaaatggaact-3', GT4R6: 5'-gtggtccag-cagccagtcaatgggc-3', GT4F3: 5'-gttcagcccgccgtacagattggc-3', and GB5: 5'-cagtagacttcacaagaggtagtgttca-3'. The Mgat4a cDNA fragments were used as probes to isolate an 11 Kb Mgat4a clone from a 129/SvJ mouse genomic DNA bacteriophage library (Stratagene, San Diego, Calif.). Chimeric mice were generated by microinjection of ES cells bearing the conditional (F, type 2) Mgat4a mutation into C57BL/6 blastocyst-stage embryos (FIG. 1C, D). Female mice bearing a germline Mgat4a$^F$ allele and the Zp3-Cre transgene were bred to acquire offspring inheriting the deleted (Δ, type 1) Mgat4a$^Δ$ allele, as described (Shafi et al., supra, 2001). In RNA expression analyses using a mouse Mgat4a cDNA probe (nt 181-339), total RNA was prepared from mouse tissues and subjected to 1% formaldehyde denaturing agarose gel electrophoresis prior to blotting as described (Metzler et al., 1994).

Mouse Breeding and Maintenance

Mice heterozygous for the Mgat4a$^Δ$ allele were backcrossed into the C57BL/6 background at least 6 generations prior to producing homozygotes for study. Mice lacking the Mgat5-encoded GnT-5 glycosyltransferase (Demetriou et al., Nature 409: 733-739, 2001) were kindly provided by James Dennis (Toronto, Ontario). All mice were housed under specific pathogen-free conditions and provided either a standard chow diet containing 16.4% protein, 73.1% carbohydrates, and 10.5% fat with 4.07 kcal/g (D12329, Research Diets, New Brunswick, N.J.)) or a high-fat chow diet containing 16.4% protein, 25.5% carbohydrates, and 58.0% fat with 5.56 kcal/g (D12331, Research Diets).

GnT-4 Enzymology

GnT-4 activity was measured in in tissue homogenates by reverse phase HPLC (Oguri et al., *J. Biol. Chem.* 272: 22721-22727, 1997) in a modification of previous methods (Nishikawa et al., *Biochim. Biophys. Acta* 1035: 313-318, 1990). The substrate GlcNAcβ1-2Manα1-6(GlcNAcβ1-2Manα1-3)Manβ1-4GlcNAcβ1-4GlcNAcβ1-2-aminopyridine was prepared as described (Tokugawa et al., *Glycoconj. J.* 13: 53-56, 1996).

Serum Chemistry

Blood was collected in the absence of anticoagulants by orbital sinus bleed or cardiac puncture and was allowed to clot for several hours in a Serum Separator Tube in which the serum was collected by centrifugation (Becton Dickinson, Mountainview, Calif.). Chemistry analyses were performed using a Beckman CX-7 automated blood chemistry analyzer with a general coefficient of variation of <5%.

Histology and Microscopy

For determining pancreatic morphology and islet abundance, 3 µm pancreatic tissue sections were stained with anti-insulin antibody (Linco Research, St. Charles, Mo.) followed by secondary HRP-conjugated anti-guinea pig antibody (ICN Biomedicals, Irvine, Calif.), and visualized using the ABC staining kit (Vector, Burlingame, Calif.). Cell nuclei were counterstained with hematoxylin. Islet cross-sectional areas were measured using KS300 software (Carl Zeiss, Jena, Germany). For immunofluorescent analyses of pancreatic islets, tissue sections were incubated with anti-Glut-2 (Chemicon, Temecula, Calif.), combined with either anti-insulin, anti-PDI (Stressgen, Victoria, Canada), anti-Calnuc (a gift from Marilyn G. Farquhar, University of California San Diego, La Jolla, Calif.), anti-adaptin γ (BD Transduction Laboratories, San Diego, Calif.), anti-EEA1 (BD Transduction Laboratories), or anti-LAMP2 (Santa Cruz Biotechnology, Santa Cruz, Calif.) at 1:200 dilution. Glut-2 was visualized using FITC-conjugated sheep anti-rabbit IgG (ICN Biomedicals Inc.). PDI, adaptin γ, EEA1, and LAMP2 were visualized with rhodamine-conjugated goat anti-mouse IgG (ICN Biomedicals Inc.). Calnuc was visualized with rhodamine-conjugated goat anti-chicken IgY (Molecular Probes, Eugene, Oreg.). Insulin was visualized with rhodamine-conjugated goat anti-guina pig IgG (ICN Biomedicals Inc.). Images were analyzed by deconvolution using a Delta Vision Restoration microscope (Applied Precision Inc., Issaquah, Wash.) and Delta Vision SoftWork software (Version 2.50).

Glucose and Insulin Homeostasis

Mice were fasted for 16 hr followed by intraperitoneal (i.p.) glucose injection (1.5 g/Kg body weight). Blood samples were obtained at 0, 30, 60, 120, and 240 min after the injection and measurements of glucose and insulin was determined, the latter using a rat insulin ELISA assay with a mouse insulin standard (Crystal Chem., Chicago, Ill.). In testing insulin tolerance, mice were injected i.p. with 2 U/kg body weight human insulin (Carbiochem, La Jolla, Calif.) followed by blood collection at 0, 30, 60 120, and 240 min after injection, and serum glucose levels were analyzed. In arginine tolerance tests, mice were fasted overnight for 16 hr followed by i.p. injection (3 g/Kg body weight) of L-arginine (Sigma, St. Louis, Mo.). Blood samples were analyzed at 0, 2, 5, 15, and 30 min after the injection.

Islet Cell Preparation and Culture

Mouse islet cells were obtained as described (Josefsen et al., J. Endocrinology 14: 145-154, 1996). Briefly, the pancreatic duct was ligated distally and injected with 3 mg/ml collagenase (Sigma), 5 µg/ml DNase (Sigma) and 5.6 mM glucose in Hank's balanced salt solution (HBSS)). The pancreas was removed and incubated for 14 min at 37° C. with shaking (200 strokes/min). The suspension was passed through a 16 gauge needle, centrifuged and suspended in the bottom layer of a discontinuous Ficoll gradient (11%, 20%, 23%, and 25%). After 15 min of centrifugation at 800× gravity at room temperature, cells were recovered from the interfaces and washed in HBSS, followed by hand selection of the islet-enriched interface under a stereomicroscope. Islets were gently dispersed after three consecutive washes with HBSS, then exposed to 0.5 U/ml of dispase (Calbiochem) in HBSS for 3 min. This was followed by gentle repetitive pipeting and a final wash with HBSS. The cells were cultured in RPMI-1640 medium containing 10% FCS, 2 mM L-glutamine, 0.1 mM 2-mercaptoethanol, and 11 mM glucose.

Flow Cytometry

Upon initial isolation, islet cells were analyzed by flow cytometry with antibodies to Glut-2 (Chemicon, Temecula, Calif.) and the insulin receptor alpha subunit (Santa Cruz Biotechnology), and were found to be between 90-95% pancreatic beta cells. Cultured islet cells (24 hrs) were harvested with ice-cold 2 mM EDTA in PBS and washed with ice-cold FACS buffer (2% FCS in PBS). Cell membranes made permeable by incubating cells with BD Cytofix/Cytoperm solution for 20 min at 4° C., and then washed twice with Perm/Wash solution (BD Biosciences Pharmingen, San Diego, Calif.). Cell labeling was carried out in 100 μl with 50,000 cells in FACS buffer on ice for 10 min. Data was acquired using a FACSCalibur Flow Cytometer and analyzed by CellQuest Software (Becton Dickinson). Antibodies to Glut-2 (Chemicon) and the insulin receptor alpha subunit (Santa Cruz Biotechnology) were used with FITC-conjugated sheep anti-rabbit IgG at 1.0 μg/ml, and 0.5 μg/ml, respectively.

In Vitro Islet Cell Glucose Transport Assay

Glucose transport into islet cells was measured using 2-[N-(7-nitrobenz-2-oxa-1,3-diazol-4-yl)amino]-2-deoxy-D-glucose (2-NBDG, Molecular Probes) as described (Yamada et al., *J. Biol. Chem.* 275: 22278-22283, 2000) Islet cells were incubated in glucose free-KRBH for 20 min at 37° C., and then with various concentrations of 2-NBDG. To measure the time course of 2-NBDG transport, islet cells were incubated with 500 μM of 2-NBDG in KRBH in the presence or absence of 10 mM D-glucose for the indicated times (FIG. 2K), then washed three times with glucose free-KRBH, and intracellular fluorescence (excitation 485-495 nm, emission 515-525 nm) was measured using a VersaFluor Fluorometer System (Bio-Rad, Hercules, Calif.). Concentration dependence was determined in same conditions except that cells were incubated with 100 μM, 200 μM, 400 μM, 800 μM, 1.6 mM, 3.2 mM, or 6.4 mM of 2-NBDG for 5 min.

Immunoprecipitation and Glycan Analyses

Isolated islets were lysed with lysis buffer (50 mM Tris-HCl, pH7.5, containing 150 mM NaCl, 1.2% Triton X-100, and proteinase inhibitor cocktail (Roche, Mannheim, Germany)), and then sonicated. Solubilized proteins were recovered in supernatant by a 15 min centrifugation at 13,000 rpm in a tabletop centrifuge at 4° C. 200 μg of total protein was subjected to immunoprecipitation with anti-Glut-2 C-terminal antibody (Santa Cruz Biotechnology). The immunoprecipitates were analyzed by immunoblotting with anti-Glut-2 antibody (Chemicon), or by lectin blotting with DSL (DSA), or L-PHA as previously described (Fukuta et al., 2000; Ye et al., 2004). Briefly, blots were rinsed with TBS, and incubated with 20 mU/ml of neuraminidase (*Vibrio choleae*, Sigma) in 50 mM sodium acetate buffer (pH 5.5) at 37° C. for 16 hours and then successively treated with 125 mU/ml of endo-β-galactosidase (*Escherichia freundii*, Calbiochem) in 50 mM sodium acetate buffer (pH 5.5) at 37° C. for 16 hours. After washing with T-TBS (0.05% Tween 20 in TBS), blots were incubated with 5% BSA in T-TBS and then probed with biotinylated DSL (2 mg/ml, Vector), or L-PHA (2 mg/ml, Vector) in T-TBS with 1% BSA. After incubating with horseradish peroxidase (HRP)-conjugated streptavidin (BD Pharmingen), the blots were washed and developed by enhanced chemiluminescence using the manufacturer's instructions (Amersham Biosciences, Buckinghamshire, England).

Pulse-Chase Analyses and Cell Surface Half-Life

Islet cells were washed twice with HBSS then incubated with RPMI 1640 medium depleted of methionine (Sigma) with 10% dialyzed fetal calf serum (Gibco/Invitrogen, Carlsbad, Calif.) for 2 hours at 37° C. Pulse labeling was performed with 400 μCi/ml [$^{35}$S]-methionine for 10 min at 37° C., and cells were then washed twice with ice-cold HBSS. Cells were either lysed directly, or returned to above culture conditions containing 2 mM cold methionine for 10, 20, 30, 40, 50, or 60 min. Cells used in chase samples were washed twice with ice-cold PBS and biotinylated with Sulfo-NHS-LC-Biotin as described above. Biotinylated proteins were purified using immobilized monomeric avidin gel (Pierce Chemical, Rockford, Ill.). Eluates isolated in the presence of D-biotin (Pierce Chemical) were incubated anti-Glut-2 C-terminal antibody. Immunoprecipitates were subjected to SDS-PAGE and gels were fixed with 30% methanol, 10% acetic acid, then treated 30 min in glacial acetic acid, another 30 min in 20% diphenyloxazol/glacial acetic acid, and finally 30 min in distilled water before drying and autoradiography at −70° C. for 3 to 7 days. For cell surface half-life analyses, islet cells were washed twice with ice-cold PBS and incubated with 1 mg/ml Sulfo-NHS-LC-Biotin (Pierce Chemical) at 4° C. for 30 min. Biotinylation was stopped by three washes of 15 mM glycine in ice-cold PBS. Cells were further cultured for 3, 6, 12, or 24 hours, then homogenized in lysis buffer, followed by immunoprecipitation using anti-Glut-2 C-terminal antibody. Glut-2 immunoprecipitates were visualized with HRP-conjugated streptavidin.

Statistical Analyses

Data was plotted as the mean±the standard error of the mean. The number (n) of samples and animals analyzed is provided and the student's t test was used to calculate indicated p values.

Exemplary GnT-4 Sequences

```
SEQ ID NO: 1 Human GnT-4a: cDNA sequence (accession number
NM_012214)
GAAATGAACCTCTCTTATTGATTTTTATTGGCCTAGAGCCAGGAGTACTGCATTCAGTTGAC

TTTCAGGGTAAAAGAAAACAGTCCTGGTTGTTGTCATCATAAACATATGGACCAGTGTGAT

GGTGAAATGAGATGAGGCTCCGCAATGGAACTGTAGCCACTGCTTTAGCATTTATCACTTCC

TTCCTTACTTTGTCTTGGTATACTACATGGCAAAATGGGAAAGAAAAACTGATTGCTTATCA

ACGAGAATTCCTTGCTTTGAAAGAACGTCTTCGAATAGCTGAACACAGAATCTCACAGCGCT

CTTCTGAATTAAATACGATTGTGCAACAGTTCAAGCGTGTAGGAGCAGAAACAAATGGAAGT

AAGGATGCGTTGAATAAGTTTTCAGATAATACCCTAAAGCTGTTAAAGGAGTTAACAAGCAA

AAAATCTCTTCAAGTGCCAAGTATTTATTATCATTTGCCTCATTTATTGAAAAATGAAGGAA
```

```
GTCTTCAACCTGCTGTACAGATTGGCAACGGAAGAACAGGAGTTTCAATAGTCATGGGCATT
CCCACAGTGAAGAGAGAAGTTAAATCTTACCTCATAGAAACTCTTCATTCCCTTATTGATAA
CCTGTATCCTGAAGAGAAGTTGGACTGTGTTATAGTAGTCTTCATAGGAGAGACAGATATTG
ATTATGTACATGGTGTTGTAGCCAACCTGGAGAAAGAATTTTCTAAAGAAATCAGTTCTGGC
TTGGTGGAAGTCATATCACCCCCTGAAAGCTATTATCCTGACTTGACAAACCTAAAGGAGAC
ATTTGGAGACTCCAAAGAAAGAGTAAGATGGAGAACAAAGCAAAACCTAGATTACTGTTTTC
TAATGATGTATGCTCAAGAAAAGGGCATATATTACATTCAGCTTGAAGATGATATTATTGTC
AAACAAAATTATTTTAATACCATAAAAAATTTTGCACTTCAACTTTCTTCTGAGGAATGGAT
GATTCTAGAGTTTTCCCAGCTGGGCTTCATTGGTAAAATGTTTCAAGCGCCGGATCTTACTC
TGATTGTAGAATTCATATTCATGTTTTACAAGGAGAAACCCATTGATTGGCTCCTGGACCAT
ATTCTCTGGGTGAAAGTCTGCAACCCTGAAAAAGATGCAAAACATTGTGATAGACAGAAAGC
AAATCTGCGAATTCGCTTCAGACCTTCCCTTTTCCAACATGTTGGTCTGCACTCATCACTAT
CAGGAAAAATCCAAAAACTCACGGATAAAGATTATATGAAACCATTACTTCTTAAAATCCAT
GTAAACCCACCTGCGGAGGTATCTACTTCCTTGAAGGTCTACCAAGGGCATACGCTGGAGAA
AACTTACATGGGAGAGGATTTCTTCTGGGCTATCACACCGATAGCTGGAGACTACATCTTGT
TTAAATTTGATAAACCAGTCAATGTAGAAAGTTATTTGTTCCATAGCGGCAACCAAGAACAT
CCTGGAGATATTCTGCTAAACACAACTGTGGAAGTTTTGCCTTTTAAGAGTGAAGGTTTGGA
AATAAGCAAAGAAACCAAAGACAAACGATTAGAAGATGGCTATTTCAGAATAGGAAAATTTG
AGAATGGTGTTGCAGAAGGAATGGTGGATCCAAGTCTCAATCCCATTTCAGCCTTTCGACTT
TCAGTTATTCAGAATTCTGCTGTTTGGGCCATTCTTAATGAGATTCATATTAAAAAAGCCAC
CAACTGATCATCTGAGAAACCAACACATTTTTTCCTGTGAATTTGTTAATTAAAGATAGTTA
AGCATGTATCTTTTTTTATTTCTACTTGAACACTACCTCTTGTGAAGTCTACTGTAGATAA
GACGATTGTCATTTCCACTTGGAAAGTGAATCTCCCATAATAATTGTATTTGTTTGAAACTA
AGCTGTCCTCAGATTTTAACTTGACTCAAACATTTTTCAATTATGACAGCCTGTTAATATGA
CTTGTACTATTTTGGTATTATACTAATACATAAGAGTTGTACATATTGTTACATTCTTTAAA
TTTGAGAAAAACTAATGTTACATACATTTTATGAAGGGGGTACTTTTGAGGTTCACTTATTT
TACTATT
```

SEQ ID NO: 2 Human GnT-4a: amino acid sequence
MRLRNGTVATALAFITSFLTLSWYTTWQNGKEKLIAYQREFLALKERLRIAEHRISQRSSEL
NTIVQQFKRVGAETNGSKDALNKFSDNTLKLLKELTSKKSLQVPSIYYHLPHLLKNEGSLQP
AVQIGNGRTGVSIVMGIPTVKREVKSYLIETLHSLIDNLYPEEKLDCVIVVFIGETDIDYVH
GVVANLEKEFSKEISSGLVEVISPPESYYPDLTNLKETFGDSKERVRWRTKQNLDYCFLMMY
AQEKGIYYIQLEDDIIVKQNYFNTIKNFALQLSSEEWMILEFSQLGFIGKMFQAPDLTLIVE
FIFMFYKEKPIDWLLDHILWVKVCNPEKDAKHCDRQKANLRIRFRPSLFQHVGLHSSLSGKI
QKITDKDYMKPLLLKIHVNPPAEVSTSLKVYQGHTLEKTYMGEDFFWAITPIAGDYILFKYD
KPVNVESYLFHSGNQEHPGDILLNTTVEVLPFKSEGLEISKETKDKRLEDGYFRIGKFENGV
AEGMVDPSLNPISAFRLSVIQNSAVWAILNEIHIKKATN SEQ ID NO: 3 Human GnT-4b: cDNA sequence (accession number NM_054013)
```
TTTTCAGAGACTCGCCTGGCAGAGGCCTGGAGCGTCCTGCTGCGTGGACTGTGGGCACCGAG
CCACCAGGAGGTTGTTGATCTCATTCTTGCTCACTGGTCCCTGCCAGACTGGTGGTGCCTCT
CTACTGTCGGGCAGCCCCACCTCTGTGCTGCCCCATCCACCTACAGCCCTCATGCCTGGGCC
```

-continued

```
CAGCTGGAGGTTCTGACAGGGGCCCCCTGGGGTGGCATGCGGACCCTTCAGGGTGCCCCAGG

CGCAGCACAGGTCTCCAGAGACACAGGCACCAGGGCGTTCAGAGCTAGTCCCCTCGCTGCTG

TTGACTGTCCTTGAGCAGCCCCAGGGCCGGTTTCTCAACCTCATTTGCTCACCTGAGCAATG

AAGTGAGGTGGGCTCCTGGAACTGCAGCAGCCACCCCCCGGGGCCATCGTGAGGCTAAGAAT

CCAGTGCAGGGTGAGCAACCAGCGACCGCTACAAGGACAGTGAAGAGCTAGCACCAGGACCT

TGGGTAGCCCACCCGCTGGAGGGAGCGTGTGCTGCAAAAAGCAAGAGTGGGCTTTGGAGGCC

AACGGATGGAGCGGATTCAGTCTGAGGCTGTTCCAGCCCTTGCTTAGGATCCACCTACCTAG

GTCTGGAAATCGTATTTCCACTTCAGATGCCTTCTCAGAGGATAAAATAACCCCCGGTGGGG

GAGAGTACTGGAAGAGGGCTAATTCCCCTGGTTTTCTCCCCATGAGCATTAGTGTCAGTGTA

ATTTTAGAGTGACCCCAGCTATGTCACGTGTGGCAGGCACAAGAACAGATGTCAATGAGCTA

TTGCAGAGGTGGACACCCAGATGTGTGCGCTGGCACACTGGAGGGGCCCGTAGGGTGGCTCT

AGACCGCCCCCTCGTGACGGCTTGCCTACCACCTGCAGGCGACGTTGTGGACGTTTACCAGC

GGGAGTTCCTGGCGCTGCGCGATCGGTTGCACGCAGCTGAGCAGGAGAGCCTCAAGCGCTCC

AAGGAGCTCAACCTGGTGCTGGACGAGATCAAGAGGGCCGTGTCAGAAAGGCAGGCGCTGCG

AGACGGAGACGGCAATCGCACCTGGGGCCGCCTAACAGAGGACCCCCGATTGAAGCCGTGGA

ACGGCTCACACCGGCACGTGCTGCACCTGCCCACCGTCTTCCATCACCTGCCACACCTGCTG

GCCAAGGAGAGCAGTCTGCAGCCCGCGGTGCGCGTGGGCCAGGGCCGCACCGGAGTGTCGGT

GGTGATGGGCATCCCGAGCGTGCGGCGCGAGGTGCACTCGTACCTGACTGACACTCTGCACT

CGCTCATCTCCGAGCTGAGCCCGCAGGAGAAGGAGGACTCGGTCATCGTGGTGCTGATCGCC

GAGACTGACTCACAGTACACTTCGGCAGTGACAGAGAACATCAAGGCCTTGTTCCCCACGGA

GATCCATTCTGGGCTCCTGGAGGTCATCTCACCCTCCCCCCACTTCTACCCTGACTTCTCCC

GCCTCCGAGAGTCCTTTGGGGACCCCAAGGAGAGAGTCAGGTGGAGGACCAAACAGAACCTC

GATTACTGCTTCCTCATGATGTACGCGCAGTCCAAAGGCATCTACTACGTGCAGCTGGAGGA

TGACATCGTGGCCAAGCCCAACTACCTGAGCACCATGAAGAACTTTGCACTGCAGCAGCCTT

CAGAGGACTGGATGATCCTGGAGTTCTCCCAGCTGGGCTTCATTGGTAAGATGTTCAAGTCG

CTGGACCTGAGCCTGATTGTAGAGTTCATTCTCATGTTCTACCGGGACAAGCCCATCGACTG

GCTCCTGGACCATATTCTGTGGGTGAAAGTCTGCAACCCCGAGAAGGATGCGAAGCACTGTG

ACCGGCAGAAAGCCAACCTGCGGATCCGCTTCAAACCGTCCCTCTTCCAGCACGTGGGCACT

CACTCCTCGCTGGCTGGCAAGATCCAGAAACTGAAGGACAAAGACTTTGGAAAGCAGGCGCT

GCGGAAGGAGCATGTGAACCCGCCAGCAGAGGTGAGCACGAGCCTGAAGACATACCAGCACT

TCACCCTGGAGAAAGCCTACCTGCGCGAGGACTTCTTCTGGGCCTTCACCCCTGCCGCGGGG

GACTTCATCCGCTTCCGCTTCTTCCAACCTCTAAGACTGGAGCGGTTCTTCTTCCGCAGTGG

GAACATCGAGCACCCGGAGGACAAGCTCTTCAACACGTCTGTGGAGGTGCTGCCCTTCGACA

ACCCTCAGTCAGACAAGGAGGCCCTGCAGGAGGGCCGCACCGCCACCCTCCGGTACCCTCGG

AGCCCCGACGGCTACCTCCAGATCGGCTCCTTCTACAAGGGAGTGGCAGAGGGAGAGGTGGA

CCCAGCCTTCGCCCCTCTGGAAGCACTGCGCCTCTCGATCCAGACGGACTCCCCTGTGTGGG

TGATTCTGAGCGAGATCTTCCTGAAAAAGGCCGACTAAGCTGCGGGCTTCTGAGGGTACCCT

GTGGCCAGCCCTGAAGCCCACATTTCTGGGGGTGTCGTCACTGCCGTCCCCGGAGGGCCAGA

TACGGCCCCGCCCAAAGGGTTCTGCCTGGCGTCGGGCTTGGGCCGGCCTGGGGTCCGCCGCT

GGCCCGGAGGCCCTAGGAGCTGGTGCTGCCCCCGCCCGCCGGGCCGCGGAGGAGGCAGGCGG
```

-continued

```
CCCCCACACTGTGCCTGAGGCCCGGAACCGTTCGCACCCGGCCTGCCCCAGTCAGGCCGTTT

TAGAAGAGCTTTTACTTGGGCGCCCGCCGTCTCTGGCGCGAACACTGGAATGCATATACTAC

TTTATGTGCTGTGTTTTTTATTCTTGGATACATTTGATTTTTTCACGTAAGTCCACATATAC

TTCTATAAGAGCGTGACTTGTAATAAAGGGTTAATGAAG
```

SEQ ID NO: 4 Human GnT-4b: amino acid sequence
```
MSRVAGTRTDVNELLQRWTPRCVRWHTGGARRVALDRPLVTACLPPAGDVVDVYQREFLALR

DRLHAAEQESLKRSKELNLVLDEIKRAVSERQALRDGDGNRTWGRLTEDPRLKPWNGSHRHV

LHLPTVFHHLPHLLAKESSLQPAVRVGQGRTGVSVVMGIPSVRREVHSYLTDTLHSLISELS

PQEKEDSVIVVLIAETDSQYTSAVTENIKALFPTEIHSGLLEVISPSPHFYPDFSRLRESFG

DPKFRVRWRTKQNLDYCFLMMYAQSKGIYYWQLEDDIVAKPNYLSTMKNFALQQPSEDWMIL

EFSQLGFIGKMFKSLDLSLIVEFILMFYRDKPIDWLLDHILWVKVCNPEKDAKHCDRQKANL

RIRFKPSLFQHVGTHSSLAGKIQKLKDKDFGKQALRKEHVNPPAEVSTSLKTYQHFTLEKAY

LREDFFWAFTPAAGDFIRFRFFQPLRLERFFFRSGNIEHPEDKLFNTSVEVLPFDNPQSDKE

ALQEGRTATLRYPRSPDGYLQIGSFYKGVAEGEVDPAFGPLEALRLSIQTDSPVWVILSEIF

LKKAD
```

SEQ ID NO: 5 Mouse GnT-4a: cDNA sequence (accession number
AB053217)
```
ATGAGGCTCCGAAATGGAACTGTGGCCACTGCGCTGGTATTTGTCACGTCCTTCCTTACCCT

ATCCTGGTATACCACGTGGCAAAATGGGAAAGAAAAACTAATTGCTTATCAACGAGAATTCC

TTGCTCTAAAAGAGCGTCTTCGAGTGGCCGAGCATAGGATATCTCAGCGCTCCTCGGAGCTA

AACACCATTGTCCAGCAGTTCCGCAGAGCTGGAGCAGAGACTAATGGAAGTAAGACAGCTCT

GAGTACAATCTCAGATAATACCATAAAGCTTCTAAAAGAGTTGACAAGCAAAAAATCACTTC

GAGTGCCAAGTATTTATTATCATTTGCCTCATCTATTGCAAAATGAAAGAAGCCTTCAGCCC

GCCGTACAGATTGGCAGTGGAAGAACGGGAGTTTCAATAGTTATGGGAATTCCTACTGTGAA

GAGAGAAGTTAAATCTTACCTCGTAGAAACCCTTCACTCCCTTATTGATAATCTGTATCCTG

AAGAGAAGCTGGACTGTGTTATAGTCGTCTTCATAGGAGAGACAGATCTTGATTATGTTCAC

AGCGTTGTTGCCAACCTGGAGAAGAATTTTCTAGAGAAATTAGTTCTGGCCTGCTGGAAAT

AATCTCTCCTCCTGAAAGCTATTACCCCGACTTGACAAACCTGAAGGAGACGTTCGGAGACT

CCAAGGAAAGAGTGAGATGGAGAACCAAGCAAAACCTGGATTACTGTTTTCTGATGATGTAT

GCTCAGGAGAAGGGCATCTACTACATTCAGCTTGAAGACGATATTATTGTCAAACAAAACTA

TTTTAATACCATAAAGAATTTTGCACTTCAACTTTCTTCGGAAGAATGGATGATTCTAGAGT

TTTCCCAGCTTGGCTTCATTGGAAAAATGTTCCAGGCGCCGGACCTGGCGCTGGTCGTGGAG

TTCATCCTCATGTTCTATAAGGAGAAGCCCATTGACTGGCTGCTGGACCACATTCTCTGGGT

GAAGGTCTGCAACCCCGAAAAAGATGCTAAACACTGCGACAGACAGAAGGCAAACCTACGAA

TCCGCTTCCGACCCTCCCTCTTCCAGCACGTGGGCCTACACTCGTCTCTGTCGGGGAAGATT

CAGAAACTCACGGATAAAGATTACATGAAGCCATTGCTTCTCAAGGTCCACGTGAACCCGCC

TGCAGAGGTCTCCACCTCCCTGAAGGTGTACCAAGGGCACACCCTGGAGAAGACCTACATGG

GGGAAGACTTCTTTTGGGCCATCACCCCCACGGCTGGAGACTACATCTTGTTTAAATTTGAC

AAACCGGTCAACGTGGAGAGTTATTGTTCCACAGCGGCAATCAAGAGCACCCAGGAGACAT

CCTGCTGAACACGACCGTGGATGTTCTCCCTCTTAAGAGCGACAGTTTGGAAATCAGCAAAG

AAACCAAAGACAAACGATTAGAAGATGGCTATTTCAGAATAGGAAAATTTGAGTATGGTGTT

GCAGAGGGAATTGTGGATCCTGGTCTAAACCCTATTTCAGCCTTTCGACTTTCCGTTATTCA
```

```
GAACTCAGCTGTTTGGGCCATTCTTAATGAGATTCATATTAAAAAGGTCACCAGTTGATCTG

CTTAGAAACCAACACGTCCTTTCTTATGACTCTTGATTAAAGATAATTAGCGCGTCCTCTTC

TGTTTGGACTGAACACTACCTCTTGTGAAGTCTACTG
```

SEQ ID NO: 6 Mouse GnT-4a: amino acid sequence
```
MRLRNGTVATALVFVTSFLTLSWYTTWQNGKEKLIAYQREFLALKERLRVAEHRISQRSSEL

NTIVQQFRRAGAETNGSKTALSTISDNTIKLLKELTSKKSLRVPSIYYHLPHLLQNERSLQP

AVQIGSGRTGVSIVMGIPTVKREVKSYLVETLHSLIDNLYPEEKLDCVIVVFIGEDYVHSVV

ANLEKEFSREISSGLLEIISPPESYYPDLTNLKETFGDSKERVRWRTKQNLDYCFLMMYAQE

KGIYYIQLEDDIIVKQNYFNTIKNFALQLSSEEWMILEFSQLGFIGKMFQAPDLALVVEFIL

MFYKEKPIDWLLDHILWVKVCNPEKDAKHCDRQKANLRIRFRPSLFQHVGLHSSLSGKIQKL

TDKDYMKPLLLKVHVNPPAEVSTSLKVYQGHTLEKTYMGEDFFWAITPTAGDYILFKFDKPV

NVESYLFHSGNQEHPGDILLNTTVDVLPLKSDSLEISKETKDKRLEDGYFRIGKFEYGVAEG

IVDPGLNPISAFRLSVIQNSAVWAILNEIHIKKVTS
```

SEQ ID NO: 7 Mouse GnT-4b: cDNA sequence (accession number AB053218)
```
ATCGGGGGAGATGAGGCTCCGCAATGGCACCTTCCTGACGCTGCTGCTCTTCTGCTTGTGCG

CCTTCCTCTCGCTCTCCTGGTACGCAGCGCTCAGCGGCCAGAAAGGTGACGTGGTGGACATT

TACCAGCGCGAGTTCCTGGCTCTGCGAGACCGTTTGCACGCGGCTGAGCAAGAGAGCCTGAA

GCGCTCCAAGGAGCTAAACCTGGTGCTGGAAGAAATCAAGAGGGCAGTATCCGAGAGGCAAG

CGCTGCGGGACGGAGAAGGCAATCGCACTTGGGGCCGCCTAACAGAGGATCCGCGACTGAAG

CCGTGGAACGTCTCGCACAGGCACGTACTTCATCTGCCCACCGTCTTCCACCATCTGCCGCA

CCTGCTGGCTAAGGAGAGCAGTCTGCAGCCCGCAGTGCGAGTGGGCCAGGGCCGCACCGGAG

TATCCGTGGTGATGGGCATTCCGAGCGTACGGCGCGAGGTGCACTCGTACTTGACTGACACA

TTGCACTCGCTCATCTCGGAGCTGAGCCCGCAGGAGAAGGAAGACTCAGTCATCGTGGTGCT

GATCGCCGAGACTGACCCACAGTACACTTCGGCAGTGACAGAGAACATCAAGGCCTTGTTCC

CCACAGAGATCCATTCTGGGCTCCTGGAAGTCATCTCCCCTTCCCCTCACTTCTACCCTGAC

TTCTCCCGCCTTCGAGAGTCCTTTGGGGACCCCAAGGAGAGAGTCAGGTGGAGGACCAAACA

GAACCTCGATTACTGCTTCCTCATGATGTATGCACAGTCCAAAGGCATCTACTATGTGCAGC

TGGAGGATGACATTGTAGCCAAGCCCAACTACTTGAGCACTATGAAGAACTTTGCCCTCCAG

CAGCCCTCCGAGGACTGGATGATCCTGGAGTTCTCGCAGTTGGGCTTCATTGGGAAGATGTT

CAAGTCACTGGATCTGAGCCTGATTGTGGAGTTCATCCTCATGTTCTACCGGGACAAGCCCA

TAGACTGGTCCTGGACCACATCCTGTGGGTGAAAGTCTGCAACCCTGAGAAGGATGCGAAA

CATTGTGATCGGCAGAAGGCCAACCTTCGGATCCGCTTCAAGCCGTCCCTTTTCCAGCATGT

GGGCACTCACTCATCACTGGCGGGCAAAATCCAGAAACTGAAGGATAAAGACTTTGGAAAGC

ATGCTCTCCGGAAGAGCTACGTGAACCCACCGGCAGAGGTGAGCACAAGCCTCAAGACGTAC

CAGCATTTCACCCTGGAGAAGGCCTACTTGCGGGAGGATTTCTTCTGGGCCTTCACACCTGC

CGCAGGAGACTTTATCCGGTTCCGCTTCTTCCAGCCACTGCGCCTTGAGCGGTTCTTCTTCC

GAAGCGGGAACATCGAGCACCCGGAAGATAAGCTCTTCAACACTTCTGTGGAGGTGCTGCCC

TTTGATAACCCCCAGTCAGAGAAGGAGGCCCTTCAGGAAGGCCGCTCAGCCACTCTCCGGTA

CCCTAGGAGCCCAGATGGATACCTCCAGATTGGCTCCTTCTACAAGGGTGTAGCTGAAGGAG

AAGTGGATCCTGCCTTTGGCCCCCTGGAAGCACTACGTCTCTCCATTCAGACTGACTCCCCG

GTGTGGGTCATTTTGAGTGAGATCTTTCTGAAAAAGGCCGACTAGAAGGCTTCCAAGGGTGC
```

```
TCTG

SEQ ID NO: 8 Mouse GnT-4b: amino acid sequence
MRLRNGTFLTLLLFCLCAFLSLSWYAALSGQKGDVVDIYQREFLALRDRLHAAEQESLKRSK

ELNLVLEEIKRAVSERQALRDGEGNRTWGRLTEDPRLKPWNVSHRHVLHLPTVFHHLPHLLA

KESSLQPAVRVGQGRTGVSVVMGIPSVRREVHSYLTDTLHSLISELSPQEKEDSVIVVLIAE

TDPQYTSAVTENIKALFPTEIHSGLLEVISPSPHFYPDFSRLRESFGDPKERVRWRTKQNLD

YCFLMMYAQSKGIYYVQLEDDIVAKPNYLSTMKNFALQQPSEDWMILEFSQLGFIGKMFKSL

DLSLIVEFILMFYRDKPIDWLLDHILWVKVCNPEKDAKHCDRQKANLRIRFKPSLFQHVGTH

SSLAGKIQKLKDKDFGKHALRKSYVNPPAEVSTSLKTYQHFTLEKAYLREDFFWAFTPAAGD

FIRFRFFQPLRLERFFFRSGNIEHPEDKLFNTSVEVLPFDNPQSEKEALQEGRSATLRYPRS

PDGYLQIGSFYKGVAEGEVDPAFGPLEALRLSIQTDSPVWVESEIFLKKAD
```

All publications, patents, accession numbers, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying an increased risk for diabetes, the method comprising identifying a mutation in an Mgat4 gene, where the mutation decreases activity of GnT-4.

* * * * *